(12) United States Patent
Donelan et al.

(10) Patent No.: US 9,057,361 B2
(45) Date of Patent: Jun. 16, 2015

(54) METHODS AND APPARATUS FOR HARVESTING BIOMECHANICAL ENERGY

(71) Applicant: Bionic Power Inc., Burnaby (CA)

(72) Inventors: James Maxwell Donelan, North Vancouver (CA); Arthur D. Kuo, Ann Arbor, MI (US); Joaquin Andres Hoffer, Anmore (CA); Qingguo Li, Burnaby (CA); Douglas Weber, Pittsburgh, PA (US)

(73) Assignee: Bionic Power Inc., Burnaby (CA)

( * ) Notice: Subject to any disclaimer, the term of this patent is extended or adjusted under 35 U.S.C. 154(b) by 160 days.

(21) Appl. No.: 13/929,542

(22) Filed: Jun. 27, 2013

(65) Prior Publication Data

US 2014/0152008 A1    Jun. 5, 2014

Related U.S. Application Data

(63) Continuation of application No. 13/648,350, filed on Oct. 10, 2012, now Pat. No. 8,487,456, which is a continuation of application No. 11/990,165, filed as application No. PCT/CA2006/001302 on Aug. 10, 2006, now Pat. No. 8,299,634.

(60) Provisional application No. 60/707,232, filed on Aug. 10, 2005.

(51) Int. Cl.
*F03G 7/08*    (2006.01)
*F03G 5/06*    (2006.01)
(Continued)

(52) U.S. Cl.
CPC .. *F03G 5/06* (2013.01); *F03G 5/00* (2013.01); *H02K 7/1853* (2013.01); *A61F 2002/708* (2013.01)

(58) Field of Classification Search
CPC ............ F03G 7/08; F03G 5/06; H02K 7/1853
USPC ................... 290/1 C, 1 E, 1 R; 623/24; 322/1
See application file for complete search history.

(56) References Cited

U.S. PATENT DOCUMENTS

| 1,184,056 A | 5/1916 | Van Deventer |
| 1,472,335 A | 5/1922 | Luzy |

(Continued)

FOREIGN PATENT DOCUMENTS

| FR | 2623086 | 5/1989 |
| JP | 5309109 | 11/1993 |

(Continued)

OTHER PUBLICATIONS

D.A. Winter, Biomechanics and motor control of human movement. 2nd ed. 1990, New York: Wiley, pp. 213-267.

(Continued)

*Primary Examiner* — Hae Moon Hyeon
(74) *Attorney, Agent, or Firm* — John R Flanagan

(57) ABSTRACT

Methods and apparatus are disclosed for harvesting energy from motion of one or more joints. Energy harvesters comprise: a generator for converting mechanical energy into corresponding electrical energy; one or more sensors for sensing one or more corresponding characteristics associated with motion of the one or more joints; and control circuitry connected to receive the one or more sensed characteristics and configured to assess, based at least in part on the one or more sensed characteristics, whether motion of the one or more joints is associated with mutualistic conditions or non-mutualistic conditions. If conditions are determined to be mutualistic, energy harvesting is engaged. If conditions are determined to be non-mutualistic, energy harvesting is disengaged.

14 Claims, 21 Drawing Sheets

(51) Int. Cl.
*F03G 5/00* (2006.01)
*H02K 7/18* (2006.01)
*A61F 2/70* (2006.01)

(56) References Cited

U.S. PATENT DOCUMENTS

| | | | |
|---|---|---|---|
| 3,358,678 A | 12/1967 | Kultsar | |
| 3,573,479 A | 4/1971 | Reith | |
| 3,631,542 A | 1/1972 | Potter | |
| 3,820,168 A | 6/1974 | Horvath | |
| 4,065,815 A | 1/1978 | Sen-Jung | |
| 4,569,352 A | 2/1986 | Petrofsky et al. | |
| 4,697,808 A | 10/1987 | Larson et al. | |
| 4,711,242 A | 12/1987 | Petrofsky | |
| 4,760,850 A | 8/1988 | Phillips et al. | |
| 4,781,180 A | 11/1988 | Solomonow | |
| 4,895,574 A | 1/1990 | Rosenberg | |
| 4,953,543 A | 9/1990 | Grim et al. | |
| 5,062,857 A | 11/1991 | Berringer et al. | |
| 5,090,138 A | 2/1992 | Borden | |
| 5,112,296 A | 5/1992 | Beard et al. | |
| 5,133,773 A | 7/1992 | Sawamura et al. | |
| 5,133,774 A | 7/1992 | Sawamura et al. | |
| 5,201,772 A | 4/1993 | Maxwell | |
| 5,282,460 A | 2/1994 | Boldt | |
| 5,344,446 A | 9/1994 | Sawamura et al. | |
| 5,358,461 A | 10/1994 | Bailey et al. | |
| 5,443,524 A | 8/1995 | Sawamura et al. | |
| 5,476,441 A | 12/1995 | Durfee et al. | |
| 5,571,205 A | 11/1996 | James | |
| 5,616,104 A | 4/1997 | Mulenburg et al. | |
| 5,628,722 A | 5/1997 | Solomonow et al. | |
| 5,888,212 A | 3/1999 | Petrofsky et al. | |
| 5,888,213 A | 3/1999 | Sears et al. | |
| 5,893,891 A | 4/1999 | Zahedi | |
| 5,917,310 A | 6/1999 | Baylis | |
| 5,980,435 A | 11/1999 | Joutras et al. | |
| 5,982,577 A | 11/1999 | Brown | |
| 5,992,553 A | 11/1999 | Morrison | |
| 6,113,642 A | 9/2000 | Petrofsky et al. | |
| 6,133,642 A | 10/2000 | Hutchinson | |
| 6,281,594 B1 | 8/2001 | Sarich | |
| 6,291,900 B1 | 9/2001 | Tiemann et al. | |
| 6,293,771 B1 | 9/2001 | Haney et al. | |
| 6,379,393 B1 | 4/2002 | Mavroidis et al. | |
| 6,423,098 B1 | 7/2002 | Biedermann | |
| 6,500,138 B1 | 12/2002 | Irby et al. | |
| 6,517,503 B1 | 2/2003 | Naft et al. | |
| 6,517,585 B1 | 2/2003 | Zahedi et al. | |
| 6,610,101 B2 | 8/2003 | Herr et al. | |
| 6,645,252 B2 | 11/2003 | Asai et al. | |
| 6,673,117 B1 | 1/2004 | Soss et al. | |
| 6,719,806 B1 | 4/2004 | Zahedi et al. | |
| 6,755,870 B1 | 6/2004 | Biedermann et al. | |
| 6,764,520 B2 | 7/2004 | Deffenbaugh et al. | |
| 6,768,246 B2 | 7/2004 | Pelrine et al. | |
| 6,770,045 B2 | 8/2004 | Naft et al. | |
| 6,852,131 B1 | 2/2005 | Chen et al. | |
| 6,910,992 B2 | 6/2005 | Arguilez | |
| 6,911,050 B2 | 6/2005 | Molino et al. | |
| 6,955,692 B2 | 10/2005 | Grundei | |
| 6,966,882 B2 | 11/2005 | Horst | |
| 7,029,500 B2 | 4/2006 | Martin | |
| 7,045,910 B2 | 5/2006 | Kitamura et al. | |
| 7,056,297 B2 | 6/2006 | Dohno et al. | |
| 7,137,998 B2 | 11/2006 | Bedard | |
| 7,147,667 B2 | 12/2006 | Bedard | |
| RE39,961 E | 12/2007 | Petrofsky et al. | |
| 7,304,398 B1 | 12/2007 | Kim et al. | |
| 7,314,490 B2 | 1/2008 | Bedard et al. | |
| 7,367,958 B2 | 5/2008 | McBean et al. | |
| 7,396,337 B2 | 7/2008 | McBean et al. | |
| 7,402,915 B2 | 7/2008 | Hutchinson et al. | |
| 7,410,471 B1 | 8/2008 | Campbell et al. | |
| 7,429,253 B2 | 9/2008 | Shimada et al. | |
| 7,431,737 B2 | 10/2008 | Ragnarsdottir et al. | |
| 7,445,606 B2 | 11/2008 | Rastegar et al. | |
| 7,485,152 B2 | 2/2009 | Haynes et al. | |
| 7,652,386 B2 | 1/2010 | Donelan et al. | |
| 7,659,636 B2 | 2/2010 | Donelan et al. | |
| 8,299,634 B2* | 10/2012 | Donelan et al. | 290/1 R |
| 8,487,456 B2* | 7/2013 | Donelan et al. | 290/1 R |
| 2001/0029343 A1 | 10/2001 | Seto et al. | |
| 2001/0029400 A1 | 10/2001 | Deffenbaugh et al. | |
| 2002/0052663 A1 | 5/2002 | Herr et al. | |
| 2003/0170599 A1 | 9/2003 | Hart | |
| 2004/0039454 A1 | 2/2004 | Herr et al. | |
| 2004/0049290 A1 | 3/2004 | Bedard | |
| 2004/0059433 A1 | 3/2004 | Slemker et al. | |
| 2004/0064195 A1 | 4/2004 | Herr | |
| 2004/0072657 A1 | 4/2004 | Arguilez | |
| 2004/0088057 A1 | 5/2004 | Bedard | |
| 2004/0102723 A1 | 5/2004 | Horst | |
| 2004/0111163 A1 | 6/2004 | Bedard et al. | |
| 2004/0181289 A1 | 9/2004 | Bedard et al. | |
| 2004/0183306 A1 | 9/2004 | Rome | |
| 2004/0186591 A1 | 9/2004 | Lang | |
| 2005/0184878 A1 | 8/2005 | Grold et al. | |
| 2006/0046907 A1 | 3/2006 | Rastegar et al. | |
| 2006/0046908 A1 | 3/2006 | Rastegar et al. | |
| 2006/0046909 A1 | 3/2006 | Rastegar et al. | |
| 2006/0046910 A1 | 3/2006 | Rastegar et al. | |
| 2006/0069448 A1 | 3/2006 | Yasui | |
| 2006/0122710 A1 | 6/2006 | Bedard | |
| 2006/0155385 A1 | 7/2006 | Martin | |
| 2006/0249315 A1 | 11/2006 | Herr et al. | |
| 2006/0260620 A1 | 11/2006 | Kazerooni et al. | |
| 2007/0016329 A1 | 1/2007 | Herr et al. | |
| 2007/0043449 A1 | 2/2007 | Herr et al. | |
| 2007/0050044 A1 | 3/2007 | Haynes et al. | |
| 2007/0056592 A1 | 3/2007 | Angold et al. | |
| 2007/0233279 A1 | 10/2007 | Kazerooni et al. | |
| 2008/0277943 A1 | 11/2008 | Donelan et al. | |
| 2008/0278028 A1 | 11/2008 | Donelan et al. | |
| 2008/0288088 A1 | 11/2008 | Langenfeld et al. | |
| 2009/0192619 A1 | 7/2009 | Martin et al. | |

FOREIGN PATENT DOCUMENTS

| | | |
|---|---|---|
| WO | 99/05991 | 2/1999 |
| WO | 01/65615 | 9/2001 |
| WO | 2004/019832 | 3/2004 |
| WO | 2006/078871 | 7/2006 |
| WO | 2006/113520 | 10/2006 |
| WO | 2007/025116 | 3/2007 |
| WO | 2007/103579 | 9/2007 |

OTHER PUBLICATIONS

Brooks, G.A., T.D. Fahey, and T.P. White, Exercise physiology: human bioenergetics and its applications. 2nd ed. 1996, Mountain View, Calif.: Mayfield Pub. iii, 750.

Bussolari, S.R. and E.R. Nadel, The physiological limits of long-duration human power production-lessons learned from the Deadalus project. Human Power, 1989. 7(4): p. 1-16.

Nadel, E.R. and S.R. Bussolari, The Daedalus Project—Physiological Problems and Solutions. American Scientist, 1988. 76(4): p. 351-360.

Niu, P., et al. Evaluation of Motions and Actuation Methods for Biomechanical Energy Harvesting. in 35th Annual IEEE Power Electronics Specialists Conference. 2004. Aachen, Germany: IEEE.

Starner, T., Human-powered wearable computing. IBM Systems Journal, 1996. 35(3-4): p. 618-629.

ThermoAnalytics, I., Battery type and characteristics. Retrieved 10 Jun. 2, 2005, from http://www.thermoanalytics.com/support/publications/batterytypesdoc.html.

Vogel, S., Prime mover: a natural history of muscle. 1st ed. 2001, New York: Norton. xi, 370 p.

Margaria, R., Biomechanics and energetics of muscular exercise. 1976, Oxford [Eng.]: Clarendon Press. x, 146 p.

Woledge, R.C., N.A. Curtin, and E. Homsher, Energetic aspects of muscle contraction. 1985, London; Orlando: Academic Press. xiii, 359.

(56) References Cited

OTHER PUBLICATIONS

Rome, L.C. et al., Generating Electricity while Walking with Loads. Science, vol. 309, p. 1725-1728, Sep. 9, 2005.
Enoka, R.M., Load-Related and Skill-Related Changes in Segmental Contributions to a Weightlifting Movement. Medicine and Science in Sports and Exercise. 1988. 20(2): p. 178-187.
Pugh, L.G., The influence of wind resistance in running and walking and the mechanical efficiency of work against horizontal or vertical forces. J Physiol, 1971. 213(2): p. 255-76.
Webb, P., et al., The Work of Walking—a Calorimetric Study. Medicine and Science in Sports and Exercise. 1988. 20(4): p. 331-337.
Donelan, J.M., R. Kram, and A.D. Kuo, Mechanical and metabolic determinants of the preferred step width in human walking. Proceedings of the Royal Society of London Series B—Biological Sciences, 2001. 268(1480): p. 1985-1992.
Donelan, J.M., R. Kram, and A.D. Kuo, Mechanical work for step-to-step transitions is a major determinant of the metabolic cost of human walking. Journal of Experimental Biology, 2002. 205(Pt 23): p. 3717-27.
Donelan, J.M., R. Kram, and A.D. Kuo, Simultaneous positive and negative external mechanical work in human walking. Journal of Biomechanics, 2002. 35(1): p. 117-124.
Gonzalez, J.L., A. Rubio, and F. Moll. A prospect on the use of piezolelectric effect to supply power to wearable electronic devices. In ICMR. 2001. Akita, Japan.
Koerner, B.I., Rise of the Green Machine, in Wired. 2005.
Hof, A.L., et al., Speed dependence of averaged EMG profiles in walking. Gait & Posture, 2002. 16(1): p. 78-86.
Kokubo, T., et al., Bioactive metals: preparation and properties. J Mater Sci Mater Med, 2004. 15(2): p. 99-107.
Thompson, C., Battery not included. Why your laptop is always running out of juice, in Slate. 2004.
Starner, T. and J.A. Paradiso, Human generated power for mobile electronics, in Low-power electronics design, C. Piguet, Editor. 2004, CRC Press: Boca Raton.
Paradiso, J.A. and T. Starner, Energy scavenging for mobile and wireless electronics, IEEE Pervasive Computing, 2005. 4(1): p. 18-27.
Whitt, F.R. and D.G. Wilson, Bicycling science. 2nd ed. 1982, Cambridge, Mass.: MIT Press. xviii, 364.
Shenck, N.S. and I.A. Paradiso, Energy scavenging with shoe-mounted piezoelectrics. IEEE Micro, 2001. 21(3): p. 30-42.
Kymissis, J., et al. Parasitic Power Harvesting in Shoes. in Second IEEE International Conference on Wearable Computing. 1998: IEEE Computer Society Press.
Antaki, J. F., et al., A gait-powered autologous battery charging system for artificial organs, Asaio J, 1995.41(3): p. M588-95.
Moll, F. and A. Rubio. An approach to the analysis of wearable body-powered systems. in MIXDES. 2000. Gdynia, Poland.
Drake, J., The greatest shoe on earth, in Wired. 2001. p. 90-100.
Soule, R.G. and R.F. Goldman, Energy Cost of Loads Carried on Head, Hands, or Feet. Journal of Applied Physiology, 1969.27(5): p. 687-&.
Saez, L.M., Energy Harvesting from Passive Human Power. PhD Thesis, Jan. 2004.
Hamilton, B., FAQ: Automotive Gasoline. Retrieved May 12, 2005.

\* cited by examiner

METHODS AND APPARATUS FOR HARVESTING BIOMECHANICAL ENERGY

RELATED APPLICATIONS

This application is a continuation of U.S. application Ser. No. 13/648,350 having a filing date of 10 Oct. 2012, which is a continuation of U.S. application Ser. No. 11/990,165 having a 35 USC §371 date of 30 Jun. 2010, which is a US national phase application of PCT/CA2006/001302 having an international filing date of 10 Aug. 2006, which in turn claims priority from, and benefit under 35 USC §119 of, U.S. application No. 60/707,232 filed 10 Aug. 2005. All of the applications described in this paragraph are hereby incorporated herein by reference.

TECHNICAL FIELD

This invention relates to methods and apparatus for converting mechanical energy generated by humans and/or animals into electrical energy. Harvested electrical energy can be used for a variety of purposes.

BACKGROUND

Humans and other animals are a rich source of mechanical power. In general, this mechanical power is derived from chemical energy. The chemical energy required for a muscle or group of muscles to perform a given activity may be referred to as the "metabolic cost" of the activity. In humans and other animals, chemical energy is derived from food. Food is generally a plentiful resource and has a relatively high energy content. Humans and other animals exhibit a relatively high efficiency when converting food into chemical energy which then becomes available to muscles for subsequent conversion into mechanical energy. Mechanical power generated by humans and other animals can be efficient, portable and environmentally friendly.

As a consequence of the attractive characteristics of human power, there have been a wide variety of efforts to convert human mechanical power into electrical power, including:

U.S. Pat. No. 1,472,335 (Luzy);
U.S. Pat. No. 1,184,056 (Van Deventer);
U.S. Pat. No. 5,917,310 (Baylis);
U.S. Pat. No. 5,982,577 (Brown);
U.S. Pat. No. 6,133,642 (Hutchinson);
U.S. Pat. No. 6,291,900 (Tiemann et al.).

A subset of the devices used to convert human mechanical power into electrical power focuses on energy harvesting—the capture of energy from the human body during everyday activities. Examples of disclosures relating to energy harvesting include:

Starner, T., *Human-powered wearable computing*. IBM Systems Journal, 1996. 35(3-4): 618-629;
Chapuis, A. and E. Jaquet, *The History of the Self-Winding Watch*. 1956, Geneva: Roto-Sadag S. A.;
Shenck, N. S. and J. A. Paradiso, *Energy scavenging with shoe-mounted piezoelectrics*. IEEE Micro, 2001. 21(3): 30-42;
Kymissis, J., et al. *Parasitic Power Harvesting in Shoes*. in Second IEEE International Conference on Wearable Computing. 1998: IEEE Computer Society Press;
Antaki, J. F., et al., *A gait-powered autologous battery charging system for artificial organs*. Asaio J, 1995. 41(3): M588-95;
Gonzalez, J. L., A. Rubio, and F. Moll. *A prospect on the use of piezolelectric effect to supply power to wearable electronic devices*. in ICMR. 2001. Akita, Japan;
Moll, F. and A. Rubio. *An approach to the analysis of wearable body-powered systems*. in MIXDES. 2000. Gdynia, Poland;
Drake, J., *The greatest shoe on earth*, in Wired. 2001. p. 90-100;
Niu, P., et al. *Evaluation of Motions and Actuation Methods for Biomechanical Energy Harvesting*. in 35*th Annual IEEE Power Electronics Specialists Conference*. 2004. Aachen, Germany: IEEE.
U.S. Pat. No. 6,768,246 (Pelrine et al.);
US patent publication No. US2004/0183306 (Rome);
U.S. Pat. No. 6,293,771 (Haney et al.);

For a variety of reasons, the energy harvesting apparatus disclosed by these authors have experienced limited power generation capacity and/or limited commercial viability or success. Drawbacks of the prior art energy harvesting apparatus contemplated in these disclosures include: lack of implementation detail; low power yield; and heavy and/or awkward energy harvesting apparatus, which can lead to relatively high metabolic energy costs and correspondingly low energy conversion efficiency and/or impairment of normal physical activity, for example.

There is a desire to provide improved methods and apparatus for harvesting biomechanical energy.

SUMMARY

One aspect of the invention provides an apparatus for harvesting energy from motion of one or more joints. In this aspect, the apparatus comprises: a generator for converting mechanical energy into corresponding electrical energy; one or more sensors for sensing one or more corresponding characteristics associated with motion of the one or more joints; and control circuitry connected to receive the one or more sensed characteristics and configured to assess, based at least in part on the one or more sensed characteristics, whether motion of the one or more joints is associated with mutualistic conditions or non-mutualistic conditions. If the control circuitry determines that the motion of the one or more joints is associated with particular mutualistic conditions, the control circuitry is configured to engage energy harvesting by completing a coupling of mechanical energy associated with the motion of the one or more joints to the generator and electrical output of the generator to a load. If the control circuitry determines that the motion of the one or more joints is associated with non-mutualistic conditions, the control circuitry is configured to disengage energy harvesting by decoupling the mechanical energy associated with the motion of the one or more joints from the generator and/or the electrical output of the generator from the load.

Another aspect of the invention provides an apparatus for harvesting energy from motion of one or more joints. In this aspect, the apparatus comprises: a generator for converting mechanical energy into corresponding electrical energy; a mechanical coupling for transferring mechanical energy associated with motion of the one or more joints to the generator; an electrical coupling for transferring electrical energy output of the generator to a load; one or more sensors for sensing one or more corresponding characteristics associated with the motion of the one or more joints; and control circuitry connected to receive the one or more sensed characteristics and configured to assess, based at least in part on the one or more sensed characteristics, whether motion of the one or more joints is associated with mutualistic conditions or non-mutualistic conditions. If the control circuitry determines that the motion of the one or more joints is associated with non-mutualistic conditions, the control circuitry is configured to disengage the mechanical energy transfer of the mechanical coupling and/or the electrical energy transfer of the electrical coupling.

Another aspect of the invention provides an apparatus for harvesting energy from motion of a joint. In this aspect, the apparatus comprises: a generator for converting mechanical energy into corresponding electrical energy; a mechanical coupling for transferring mechanical energy associated with motion of the joint to the generator; and an electrical coupling for transferring electrical energy output of the generator to a load. The joint may be the knee joint.

Another aspect of the invention provides a method for harvesting energy from motion of one or more joints. In this aspect, the method comprises: providing a generator for converting mechanical energy into corresponding electrical energy; sensing one or more characteristics associated with motion of the one or more joints; and assessing, based at least in part of the one or more sensed characteristics, whether motion of the one or more joints is associated with mutualistic conditions or non-mutualistic conditions. If the motion of the one or more joints is determined to be associated with particular mutualistic conditions, energy harvesting is engaged by completing a coupling of mechanical energy associated with the motion of the one or more joints to the generator and electrical output of the generator to a load. If the motion of the one or more joints is determined to be associated with non-mutualistic conditions, then energy harvesting is disengaged by decoupling the mechanical energy associated with the motion of the one or more joints from the generator and/or the electrical output of the generator from the load.

Another aspect of the invention provides a method for harvesting energy from motion of a joint. In this aspect, the method comprises: providing a generator for converting mechanical energy into corresponding electrical energy; mechanically coupling the joint to the generator to transfer mechanical energy from the joint to the generator; and electrically coupling the electrical energy output from the generator to a load. The joint may comprise the knee joint.

Another aspect of the invention provides an apparatus for harvesting energy from motion of one or more joints. In this aspect, the apparatus comprises: means for converting mechanical energy associated with the motion of the one or more joints into electrical energy; means for assessing whether the motion of the one or more joints is associated with mutualistic conditions or non-mutualistic conditions; means for completing a coupling of mechanical energy associated with the motion of the one or more joints to the converting means and electrical output of the converting means to a load if the assessing means determines that the motion of the one or more joints is associated with particular mutualistic conditions; and means for disengaging the mechanical energy associated with the motion of the one or more joints from the converting means and/or electrical output of the converter from the load, if the assessing means determines that the motion of the one or more joints is associated with non-mutualistic conditions.

Another aspect of the invention provides an apparatus for harvesting energy from motion of one or more joints. In this aspect, the apparatus comprises: a generator coupled to the one or more joints and to a load for converting mechanical energy associated with motion of the one or more joints into corresponding electrical energy delivered to the load; one or more sensors for sensing one or more corresponding characteristics associated with motion of the one or more joints; and control circuitry connected to receive the one or more sensed characteristics and configured to assess, based at least in part on the one or more sensed characteristics, whether motion of the one or more joints is associated with mutualistic conditions or non-mutualistic conditions. If the control circuitry determines that the motion of the one or more joints is associated with non-mutualistic conditions, the control circuitry is configured to decouple the generator from the one or more joints and/or the generator from the load.

Another aspect of the invention provides a method for harvesting energy from motion of one or more joints. In this aspect, the method comprises: providing a generator coupled to the one or more joints and to a load for converting mechanical energy associated with motion of the one or more joints into corresponding electrical energy delivered to the load; sensing one or more characteristics associated with motion of the one or more joints; and assessing, based at least in part of the one or more sensed characteristics, whether motion of the one or more joints is associated with mutualistic conditions or non-mutualistic conditions. If the motion of the one or more joints is determined to be associated with non-mutualistic conditions, then the method comprises decoupling the generator from the one or more joints and/or the generator from the load.

Further aspects of the invention, further features of specific embodiments of the invention and applications of the invention are described below.

BRIEF DESCRIPTION OF DRAWINGS

In drawings which show non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the disclosure. Accordingly, the specification and drawings are to be regarded in an illustrative, rather than a restrictive, sense.

Figure 1A:
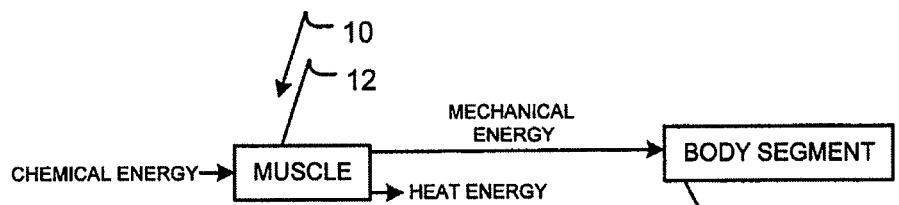
FIG. 1A schematically depicts a positive mechanical operational mode of a muscle wherein the muscle is used to generate movement of one or more associated body segment(s)

FIG. 1A schematically depicts a positive mechanical power operational mode 10 of a muscle 12, wherein muscle 12 is used to generate mechanical energy which results in corresponding movement of one or more associated body segment(s) 44 (e.g. limb(s)). In positive mechanical power mode 10, muscle 12 converts chemical energy into mechanical energy of associated body segment 44. Due to the inefficiency of this conversion process, muscle 12 also outputs heat energy when operating in positive mechanical power mode 10. Positive mechanical power mode 10 is associated with the shortening of muscle 12. Shortening of muscle 12 can pull associated body segment 44 around a joint (not shown), for example. For some activities, the efficiency of positive power production can approach 25%. With such an efficiency, for muscle 12 to generate 1 W of mechanical power requires a metabolic cost of 4 W and the remaining 3 W is dissipated as heat.

Figure 1B:
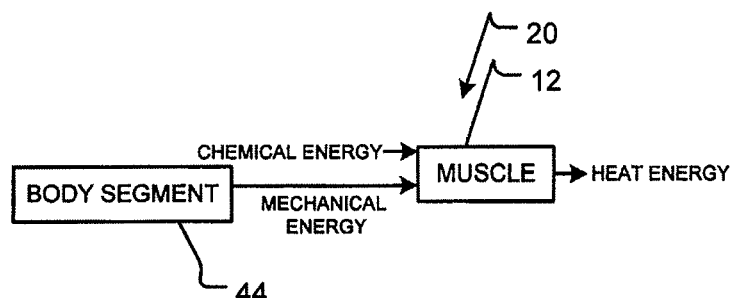
FIG. 1B schematically depicts a negative mechanical operational mode of a muscle wherein the muscle is used to decelerate movement of one or more associated body segment(s)

FIG. 1B schematically depicts a negative mechanical power operational mode 20 of muscle 12, wherein muscle 12 acts to brake (i.e. decelerate) the motion of the associated body segment(s) 44, thereby reducing the mechanical energy of body segment 44 and causing body segment 44 to decelerate. Muscle 12 requires chemical energy to cause this braking effect. In negative mechanical power mode, muscle 12 uses chemical energy to reduce the mechanical energy of the associated body segment and, in doing so, produces heat energy. Negative mechanical power mode 20 is associated activity in a particular muscle 12 when that muscle 12 is lengthening. During negative mechanical power mode, muscle 12 is actively generating force which tends to decelerate a lengthening of muscle 12. When muscle 12 operates in a negative mechanical power mode, associated body segment 44 may be moving around a joint in a direction that causes muscle 12 to lengthen, but the activity of muscle 12 causes deceleration of the rate of movement of associated body segment 44. For some activities, the efficiency associated with negative power production can be as high as −120%. With such an efficiency, for muscle 12 to produce −1 W of mechanical power requires a metabolic cost of 0.83 W and 1.83 W is dissipated as heat.

Figure 2:
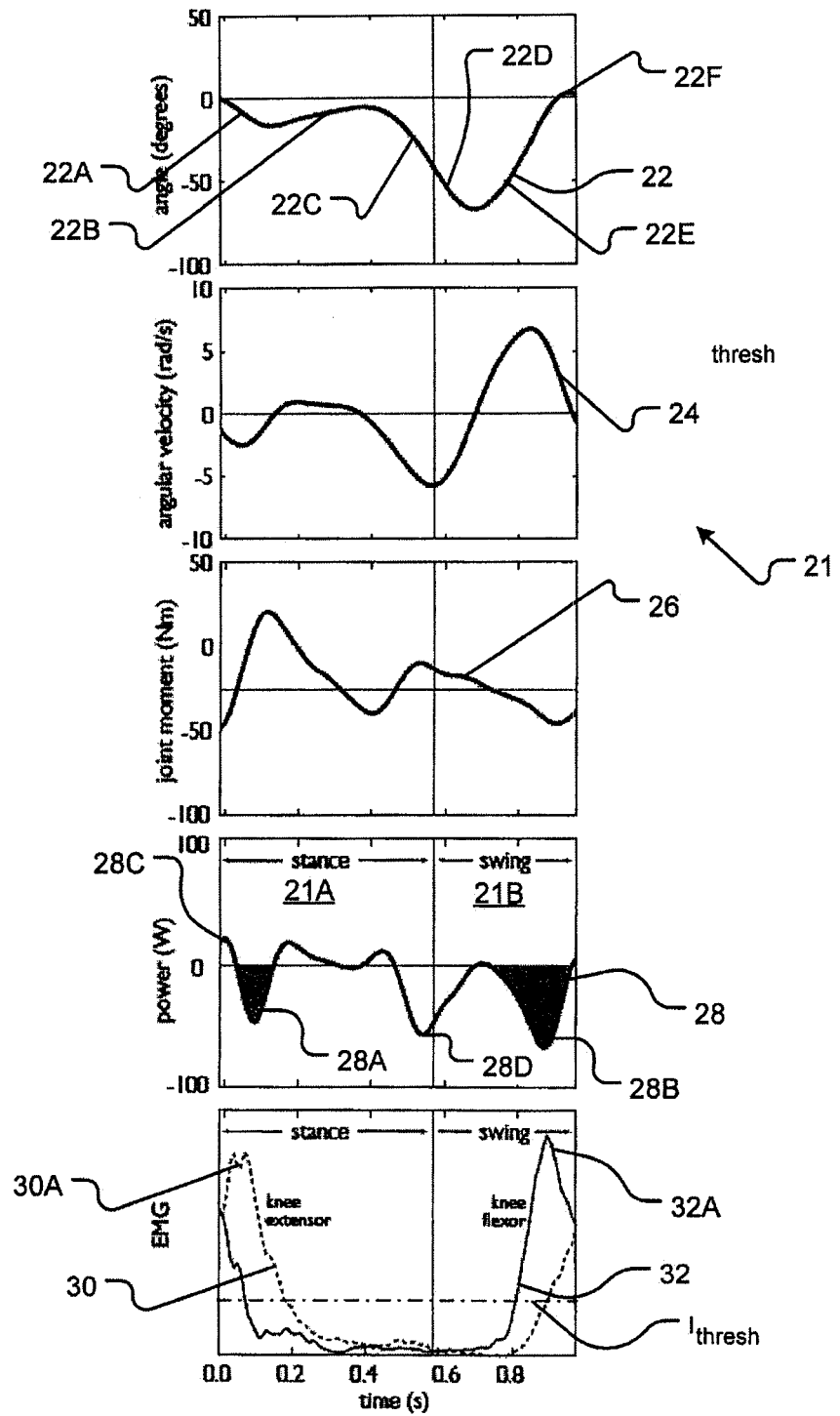
FIG. 2 shows a number of plots representative of various quantities relating to the typical dynamics of a knee joint during one full cycle of a walking movement.

During many activities, especially rhythmic activities like walking or running, muscles switch frequently between positive and negative mechanical power generation modes. Because muscles act on the body's skeletal system, positive and negative muscle power may be seen (from an external perspective), as positive and negative joint power. FIG. 2 presents a number of plots representative of various quantities relating to typical dynamics of a knee joint during one full cycle 21 of a walking movement for a 58 kg subject walking at 1.3 m/s with a step frequency of 1.8 Hz:

Plot 22 represents the angle of the knee joint, where 0° represents full extension and negative angles represent knee flexion;

plot 24 represents the angular velocity of the knee joint (i.e. the time derivative of plot 22), where positive angular velocity represents movement in the knee extension direction and negative angular velocity represents movement in the knee flexion direction;

plot 26 represents the moment of the knee joint, where a positive moment represents torque in the extension direction and a negative moment represents torque in the flexion direction;

plot 28 represents the mechanical power associated with the knee joint. Mechanical power (plot 28) represents the product of the torque (plot 26) and the angular velocity (plot 24) of the knee joint. The integral of the mechanical power (plot 28) represents the mechanical work performed by the knee joint;

plot 30 represents rectified and filtered electromyographic (EMG) signals representative of electrical activity generated by the vastus lateralis (i.e. one of the quadricep muscles) which is an example of a knee extensor muscle; and plot 32 represents rectified and filtered EMG signals representative of electrical activity generated by the semitendinosus (i.e. one of the hamstrings) which is an example of a knee flexor muscle.

Referring to FIG. 2, cycle 21 may generally be divided into a stance phase 21A, where the foot corresponding to the illustrated knee is on the ground, and a swing phase 21B, where the foot corresponding to the illustrated knee is off of the ground. In the illustrated plots, heel strike occurs at time t=0, where plot 22 shows that the knee is almost at full extension. At time t=0, the leg corresponding to the illustrated knee extends forwardly from the hip and represents the front one of the two legs. Immediately after time t=0, the knee begins to flex in region 22A as weight is transferred to the corresponding leg. In region 22B, the illustrated knee rebounds and extends slightly during the swing phase of the other leg. In region 22C, the illustrated knee begins to flex again as it prepares for swing phase 21B. In region 22D, cycle 21 enters swing phase 21B and the foot corresponding to the illustrated knee leaves the ground. The illustrated knee continues to flex in region 22D. In region 22E, the knee begins to extend again as the corresponding leg swings forwardly again and prepares for another heel strike. In region 22F, the illustrated knee is relatively straight. The knee may extend slightly beyond straight in region 22F immediately before heel strike which marks the beginning of the next cycle.

Regions 28A and 28B of power plot 28 represent regions where at least some of the muscles associated with the illustrated knee are in negative mechanical power modes 20 (see FIG. 1B). In region 28A, the illustrated knee is flexing and the knee extensor muscles are lengthening, but at least the illustrated knee extensor muscles are acting in a negative mechanical power mode 20 to counteract this flexion movement. Region 30A of plot 30 shows how the illustrated knee extensor muscles are active during the time associated with region 28A. In region 28B, the illustrated knee is extending and the knee flexor muscles are extending, but at least the illustrated knee flexor muscles are acting in a negative mechanical power mode 20 to counteract this extension movement. Region 32A of plot 32 shows how the illustrated knee flexor muscles are active during the time associated with region 28B.

In some embodiments of the invention, methods and apparatus are provided for selectively harvesting energy from the movement of particular joints when the muscles associated with the particular joints are operating in negative mechanical power modes 20 (i.e. when muscles would normally be active to decelerate movement of the joints). Selectively harvesting energy from the movement of particular joints when the muscles associated with the particular joints are operating in a negative mechanical power mode 20 is referred to herein as "mutualistic" energy harvesting. In particular embodiments, the harvested energy is output as electrical power. The term mutualistic is appropriate because the mechanical power used to generate electric power under mutualistic conditions can come from the decelerating joints and the harvesting of energy under mutualistic conditions actually assists the muscles to decelerate the joints.

Figure 3A:
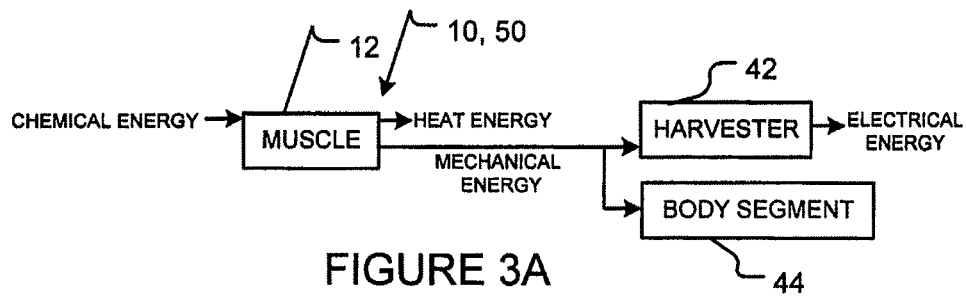
FIG. 3A schematically depicts non-mutualistic energy harvesting during a positive mechanical power mode of an associated muscle.
Figure 3B:
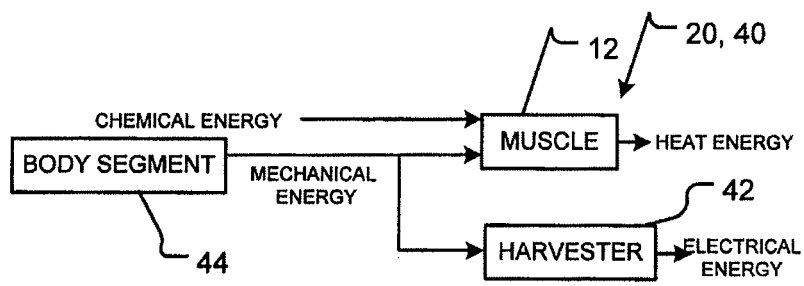
FIG. 3B schematically depicts mutualistic energy harvesting during a negative mechanical power mode of an associated muscle.

FIG. 3B schematically illustrates mutualistic energy harvesting 40 when muscle 12 is operating in a negative mechanical power mode 20. As discussed above in relation to FIG. 1B, when muscle 12 is operating in negative mechanical mode 20, muscle 20 consumes metabolic (chemical) energy in an effort to reduce the mechanical energy of one or more associated body segment(s) 44 (i.e. cause body segment 44 to decelerate) and outputs heat energy during this process. As shown in FIG. 3B, when harvesting energy in a mutualistic manner 40, a harvester 42 helps to reduce the mechanical energy of associated body segment 44 (i.e. cause body segment 44 to decelerate) by converting the mechanical energy of associated body segment 44 into electrical energy. Rather than using energy from muscle 12 alone to cause body segment 44 to decelerate, harvester 42 helps to cause body segment 44 to decelerate and in doing so converts mechanical energy to electrical energy. Accordingly, mutualistic energy harvesting may actually decrease the metabolic costs associated with decelerating the motion of body segment 44. Harvester 42 may comprise a generator, for example, and the mechanical energy required to turn the generator may be obtained from movement of associated body segment 44 as it decelerates.

When selectively harvesting energy in a mutualistic mode 40, muscle 12 requires less metabolic (chemical) energy, because part of the negative power required to cause body segment 44 to decelerate is provided by harvester 42. Accordingly, selectively harvesting energy in a mutualistic mode 40 can actually reduce the metabolic cost and/or effort normally experienced by a person when performing an activity. For example, assuming that harvester 42 has a 50% mechanical to electrical conversion efficiency, then extracting 1 W of electrical power from harvester 42 would require 2 W of mechanical energy, meaning that the mechanical energy reduction performed by muscle 12 would be 2 W less. Assuming that muscle 12 operates with the above-discussed −120% efficiency in negative mechanical power mode 20, then a 2 W reduction in mechanical energy corresponds approximately to a 1.7 W reduction in metabolic (chemical) energy consumed by muscle 12.

In some embodiments, energy harvesting methods and apparatus also harvest energy from the movement of particular joints when the muscles associated with the particular joints are operating in positive mechanical power modes 10 (i.e. when muscles are active to generate movement of the body). Harvesting energy from the movement of particular joints when the muscles associated with the particular joints are operating in a positive mechanical power mode 20 is referred to herein as "non-mutualistic" energy harvesting. Non-mutualistic energy harvesting generally requires increased metabolic costs (i.e. chemical energy) from the muscles. For this reason, non-mutualistic energy harvesting may also be referred to as "parasitic" energy harvesting.

FIG. 3A schematically illustrates non-mutualistic energy harvesting 50 when muscle 12 is operating in a positive mechanical power mode 10. As discussed above in relation to FIG. 1A, when muscle 12 is operating in positive mechanical mode 10, muscle 20 consumes metabolic energy in an effort to generate mechanical energy in one or more associated body segment(s) 44 (i.e. to cause body segment(s) 44 to move) and outputs heat energy during this process. As shown in FIG. 3A, when harvesting energy in a non-mutualistic manner 50, harvester 42 requires additional mechanical energy generated by muscle 12 and associated with movement of body segment 44 to provide electrical energy. In contrast to mutualistic energy harvesting 40, non-mutualistic energy harvesting 50 requires that the user work harder (i.e. to exert more effort) in order to generate electrical energy. For example, assuming that harvester 42 has a 50% mechanical to electrical conversion efficiency, then extracting 1 W of electrical power from harvester 42 would require 2 W of mechanical energy, meaning that muscle 12 would have to provide an additional 2 W of mechanical energy. Assuming that muscle 12 operates with the above-discussed 25% efficiency in positive mechanical power mode 10, then a 2 W increase in mechanical energy production corresponds to an 8 W increase in the metabolic (chemical) energy consumed by muscle 12. The increased metabolic cost and/or effort of non-mutualistic energy harvesting relative to mutualistic energy harvesting tends to limit the maximum power available from non-mutualistic energy harvesting and the duration over which energy can be harvested.

In some embodiments where it is desired to harvest energy mutualistically, methods and apparatus are provided which incorporate one or more feedback-providing sensors. Feedback from such sensors can be used to make decisions as to whether particular muscle(s) is/are operating in a negative mechanical power mode 20, thus permitting selective engagement and disengagement of the generator for mutualistic energy harvesting 40 and for avoiding, to the extent possible, non-mutualistic energy harvesting 50.

In some embodiments, methods and apparatus are provided for selective mutualistic energy harvesting of the energy associated with knee motion when a person is walking. As discussed above in relation to typical walking cycle 21 of FIG. 2, each walking cycle involves:

a period of time (region 28A) near the beginning of stance phase 21A, where the knee is flexing as the weight of the body is being transferred to the corresponding leg and the knee extensor muscles operate in a negative mechanical power mode to receive this weight and decelerate this flexion; and a period of time (region 28B) near the end of swing phase 21B, where the knee is extending and the knee flexor muscles operate in a negative mechanical power mode to decelerate this flexion.

As illustrated in FIG. 2, substantial power may be available in regions 28A, 28B at normal walking speeds. This available power will tend to increase for a heavier person or when a person is walking faster or when a person is walking downhill.

FIG. 2 also shows another region 28D at the end of stance phase 21A and the beginning of swing phase 21B, where the knee is flexing and exhibits negative power. However, it can be seen from plot 30, that the illustrated knee extensor muscles are not active during the time associated with region 28D. Those skilled in the art will appreciate that region 28D represents a period of positive mechanical power operation with the muscles associated with the ankle (i.e. movement of the ankle). Some of the ankle muscles (e.g. the gastrocnemius) cross the knee joint. A potential consequence of harvesting energy from knee joint motion in region 28D is interference with the positive mechanical power operation of these muscles with respect to the ankle joint. Harvesting energy in region 28D may be non-mutualistic because of the increase in metabolic cost associated with interfering with the positive power operational mode of the muscles that cross both the ankle and knee joints. In general, it is desirable to consider the function of individual muscles when considering whether to harvest energy.

Figure 4A:
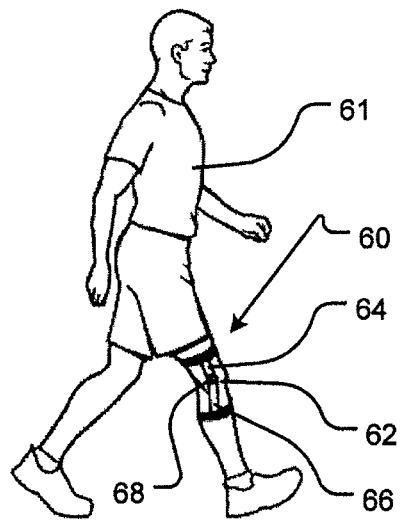
FIG. 4A shows an energy harvesting apparatus according to a particular embodiment of the invention wherein the energy harvester is mountable on the body of a host.
Figure 4B:
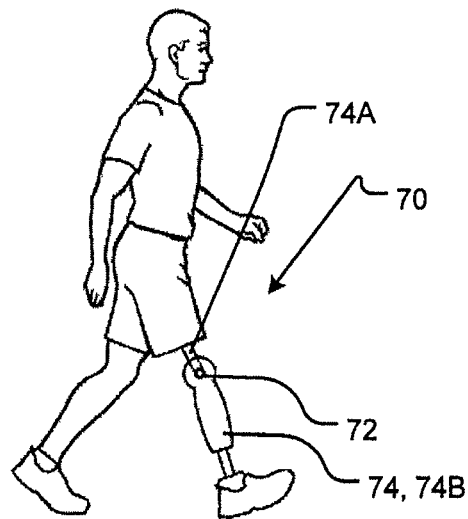
FIG. 4B shows an energy harvesting apparatus according to another embodiment of the invention wherein the energy harvester is embedded in a prosthetic limb.
Figure 4C:
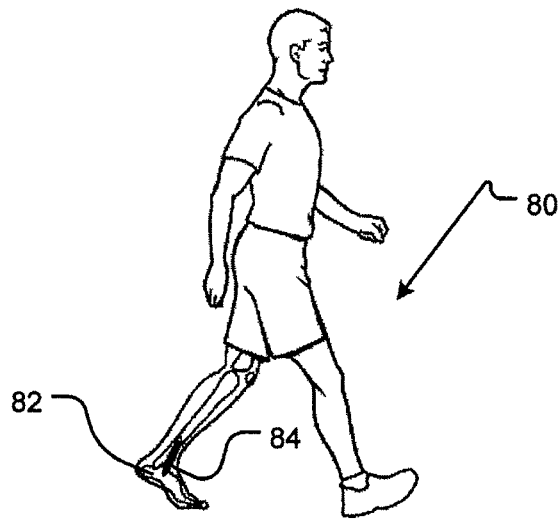
FIG. 4C shows an energy harvesting apparatus according to another embodiment of the invention wherein the energy harvester is implanted under the skin of the host.

FIGS. 4A, 4B and 4C depict a number of different exemplary embodiments of the invention. FIG. 4A shows a wearable energy harvesting apparatus 60 according to a particular embodiment of the invention. In the illustrated embodiment, harvesting apparatus 60 operates to harvest energy from the motion of knee joint 62 and the corresponding knee extensor muscles and knee flexor muscles. FIG. 4B shows an energy harvesting apparatus 70 according to another embodiment of the invention that is embedded in a prosthetic limb 74. In the illustrated embodiment, prosthetic limb 74 incorporates a joint 72 which is intended to emulate a knee joint. In the illustrated embodiment, harvesting apparatus 70 operates to harvest energy from the motion of joint 72. FIG. 4C shows an energy harvesting apparatus 80 according to yet another embodiment of the invention that is implanted under the skin of the host to harvest energy from the motion of ankle joint 82 and its corresponding ankle flexor and extensor muscles (e.g. the tibialis anterior).

Energy harvesting apparatus 60 (FIG. 4A) can be mounted to and/or worn on the body 61 of a human. In the illustrated embodiment, apparatus 60 is mounted across knee joint 62 with an upper component 64 located above knee joint 62, a lower component 66 located below knee joint 62 and a pivot joint 68 located generally coaxially with knee joint 62. When the host (i.e. the person to whom apparatus 60 is mounted) bends knee joint 62, pivot joint 68 pivots allowing corresponding relative movement between upper component 64 and lower component 66. Energy harvester 60 may be designed to harvest energy during extension of knee joint 62, during flexion of knee joint 62 or during both extension and flexion. In other embodiments, energy harvesting apparatus can be configured to be mounted across other joints, such as the ankle, wrist or elbow, for example. In other embodiments, energy harvesting apparatus may extend across a plurality of joints, such as the knee and the ankle or the elbow and the shoulder for example.

Figure 5A:
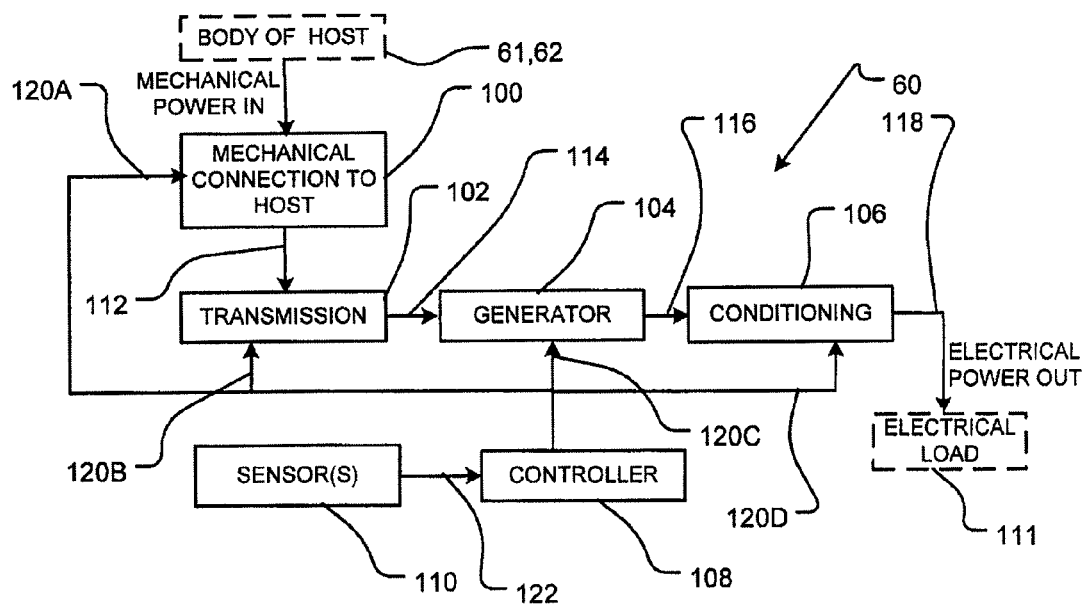
FIG. 5A is a schematic block diagram of an energy harvesting apparatus according to a particular embodiment of the invention.

FIG. 5A is a schematic block diagram of energy harvesting apparatus 60 according to a particular embodiment of the invention. Energy harvesting apparatus 60 comprises a transmission 102 which is mechanically connected to the body 61 of a host via a mechanical connection 100. In the illustrated embodiment, connection 100 connects the knee 62 of the host to transmission 102. Connection 100 transfers mechanical power (represented by line 112) from knee 62 to transmission 102. Connection 100 may comprise one or more of upper and lower components 64, 66 and pivot joint 68 (see FIG. 4A). In other embodiments, connection 100 may be provided by other suitably configured mechanisms. Transmission 102 transforms mechanical power 112 received from connection 100 into a different form of mechanical power (represented by line 114) suitable for use by generator 104. In some embodiments, transmission 102 converts relatively high-torque, low-speed mechanical power (e.g. the type of mechanical power produced by knee joint 62) into relatively low-torque, high-speed mechanical power which is suitable for use by generator 104.

Generator 104 converts mechanical power 114 into electrical power signal 116. Depending on the nature of mechanical power input 114 and generator 104, electrical power signal 116 may have a variety of forms. Accordingly, in the illustrated embodiment, energy harvesting apparatus 60 comprises a signal conditioner 106 which conditions electrical power signal 116 to generate an electrical power output signal 118. Electrical power output signal 118 output by signal conditioner 106 is supplied to an electrical load 111. Electrical load 111 may comprise any one or more components capable of using and/or storing electrical power from output signal 118. Non-limiting examples of suitable electric loads 111 include electronic devices (e.g. personal electronic devices) and battery chargers.

Energy harvester 60 also comprises a controller 108 which receives a feedback signal 122 from one or more sensors 110. Controller 108 may comprise one or more data processors, together with suitable hardware, including, by way of non-limiting example: accessible memory, logic circuitry, drivers, amplifiers, A/D and D/A converters and the like. Controller 108 may comprise, without limitation, a microprocessor, a computer-on-a-chip, the CPU of a computer or any other suitable microcontroller. Controller 108 may comprise a plurality of data processors.

Feedback signal 122 preferably provides controller 108 with information that may be used by controller 108 to determine whether or not conditions are suitable for mutualistic energy harvesting. Sensor(s) 110 may comprise a wide variety of sensors and may detect, by way of non-limiting example, positions of the body of the host (e.g. one or more limbs or other body segments), positions and/or activity levels of muscles, positions and/or configurations of generator 104, transmission 102 and/or connection 100. Non-limiting examples of sensor(s) which may be suitable for sensor(s) 110 include potentiometers, accelerometers, rate gyroscopes, position encoders, inclinometers, pressure sensors or the like that detect contact of a body segment with another object (e.g. the ground). Sensor(s) 110 may comprise signal conditioning circuitry (not shown) that is well known to those skilled in the art for providing a signal suitable for use by controller 108. By way of non-limiting example, such circuitry may comprise amplifiers, analog to digital A/D converters, filters and the like.

Controller 108 may make use of the information contained in feedback signal 122 to determine whether or not conditions are suitable for mutualistic energy harvesting. In some embodiments, controller 108 is configured, or may be configured (e.g. by user input), to cause harvester 60 to harvest energy primarily under conditions considered by controller 108 to be mutualistic. In such embodiments, controller 108 couples body 61 (e.g. knee 62) to electrical load 111 under conditions which controller 108 determines to be mutualistic and disengages body 61 (e.g. knee 62) from electrical load 111 under conditions which controller 108 determines to be non-mutualistic.

Controller 108 may use a wide variety of techniques to couple body 61 to electrical load 111 under mutualistic conditions and/or decouple body 61 from electrical load 111 under non-mutualistic conditions. Techniques for coupling body 61 to, and decoupling body 61 from, load 111 can involve mechanical coupling/decoupling. For example, controller 108 may use signal 120A to cause connection 100 to be mechanically coupled to body 61 under mutualistic conditions and to cause connection 100 to be mechanically decoupled from body 61 under non-mutualistic conditions. Controller 108 may additionally or alternatively use signal 120A and/or signal 120B to control the operation of connection 100 and/or transmission 102, such that connection 100 and transmission 102 are mechanically coupled to one another under mutualistic conditions and are mechanically decoupled from one another under non-mutualistic conditions. Controller 108 may additionally or alternatively use signal 120B and/or signal 120C to control the operation of transmission 102 and/or generator 104, such that transmission 102 and generator 104 are mechanically coupled to one another under mutualistic conditions and are mechanically decoupled from one another under non-mutualistic conditions. By way of non-limiting example, such mechanical coupling and decoupling (e.g. between connection 100 and transmission 102 and/or between transmission 102 and generator 104) may be accomplished using a suitably configured clutch which is responsive to one or more of signals 120A, 120B, 120C or a suitably configured locking mechanism that is responsive to one or more of signals 120A, 120B, 120C.

In embodiments where it is desired to harvest energy primarily under conditions considered by controller 108 to be mutualistic, controller 108 may additionally or alternatively use electrical coupling/decoupling mechanisms for coupling body 61 to, and decoupling body 61 from, load 111. For example, controller 108 may use signal 120C and/or signal 120D to electrically connect generator 104 to conditioning circuitry 106 under mutualistic conditions and to electrically disconnect generator 104 from conditioning circuitry 106 under non-mutualistic conditions. Controller 108 may additionally or alternatively use signal 120D to electrically connect conditioning circuitry 106 to electrical load 111 under mutualistic conditions and to electrically disconnect conditioning circuitry 106 from electrical load 111 under non-mutualistic conditions. By way of non-limiting example, such electrical coupling and decoupling (e.g. between generator 104 and conditioning circuitry 106 and/or between conditioning circuitry 106 and load 111) may be accomplished using a suitably configured electrical switch which is responsive to one or more of signals 120C, 120D.

In some embodiments, controller 108 is configured, or may be configured (e.g. by user input), to cause harvesters 60 to harvest energy under mutualistic and non-mutualistic conditions. Where it is desired to continually harvest energy under mutualistic and non-mutualistic conditions, controller 108 and sensors 110 are not generally required. In some embodiments, signals 120A, 120B and/or 120C may be used by controller 108 to control other aspects of the operation of connection 100, transmission 102 and/or generator 104. Controller 108 may also optionally control the operation of signal conditioner 106 using signal 120D. In the illustrated embodiment, signals 120A, 120B, 120C, 120D comprise one way signals, but, in other embodiments, signals 120A, 120B, 120C, 120D comprise two-way signals.

In some embodiments, controller 108 is configured, or may be configured (e.g. by user input), to turn off harvester 60 (i.e. so that harvester 60 stops harvesting activity altogether until it is activated again).

Figure 5B:
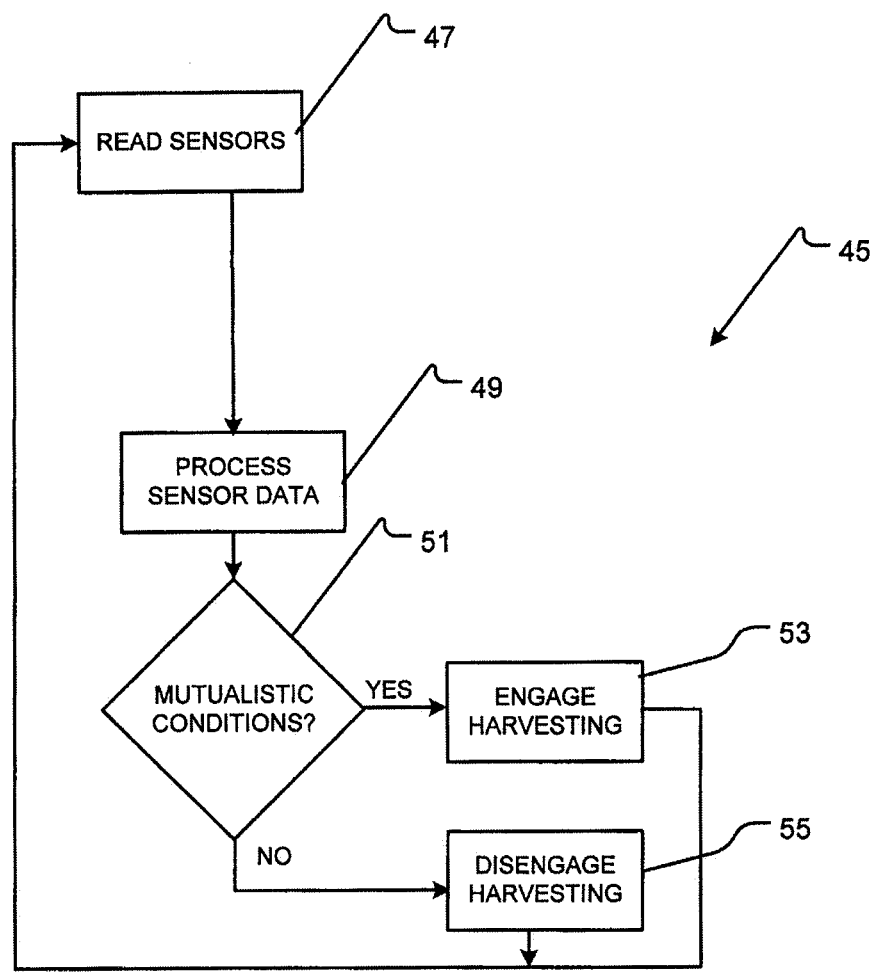
FIG. 5B is a schematic block diagram showing a method for determining when to engage the FIG. 5A energy harvesting apparatus to harvest energy under mutualistic conditions according to a particular embodiment of the invention.

FIG. 5B is a schematic block diagram showing a method 45 for determining when to engage the FIG. 5A energy harvesting apparatus to harvest energy under mutualistic conditions according to a particular embodiment of the invention. Method 45 begins in block 47 where controller 108 obtains feedback 122 from sensor(s) 110. As discussed above, controller 108 makes use of feedback data 122 (which may include present and historical feedback data 122) to make a decision as to whether conditions are mutualistic such that energy should be harvested. In block 49, method 45 involves processing feedback data 122. The block 49 processing may comprise filtering, scaling, offsetting or otherwise digitally manipulating the incoming angular position data, for example. In some embodiments, some of the block 49 processing may occur in the analog domain (i.e. prior to the block 47 data acquisition).

Method 45 then proceeds to block 51 which involves an inquiry into whether or not controller 108 considers the conditions to be mutualistic. In some embodiments, the block 51 inquiry comprises considering a model of the motion associated with one or more joints (e.g. knee 62) and using the model together with measured characteristics associated with the one or more joints (e.g. feedback data 122) to determine whether conditions are mutualistic. In some embodiments, the block 51 inquiry additionally or alternatively comprises direct measurement or sensing of muscle activity to determine whether conditions are mutualistic. The block 51 inquiry may comprise assessing whether: (i) one or more muscles associated with the one or more joints are acting to decelerate motion of the one or more joints; (ii) one or more muscles associated with the one or more joints are producing torque in a particular direction and the one or more joints are moving in the opposing direction; (iii) one or more muscles associated with the one or more joints are extending and the same one or more muscles are active; and/or (iv) one or more muscles associated with the one or more joints are otherwise operating in a negative mechanical power operational mode.

The block 51 inquiry may also involve an optional inquiry into whether there is some reason that controller 108 should not cause energy to be harvested even though conditions appear to be mutualistic. Such an inquiry may involve knowledge of particular types of movement of the one or more joints and/or the one or more associated muscles. By way of example, controller 108 may determine, during such an inquiry, that it is not desirable to harvest energy from knee 62 during region 28D of the walking cycle (see FIG. 2) even though one or more muscles associated with knee 62 are operating in a negative mechanical power operational mode. As discussed above, negative power operation of some muscles associated with knee motion in region 28D may be accompanied by positive power operation of the same muscles associated with ankle motion.

If controller 108 determines in block 51 that conditions are mutualistic (block 51 YES output), then method 45 proceeds to block 53 where controller 108 causes an appropriate one or more of signals 120A, 120B, 120C, 120D to couple body 61 to electrical load 111, thereby engaging energy harvesting. If controller 108 determines in block 51 that conditions are non-mutualistic (block 51 NO output), then method 45 proceeds to block 55 where controller 108 causes an appropriate one or more of signals 120A, 120B, 120C, 120D to decouple body 61 from electrical load 111, thereby disengaging energy harvesting. Method 45 then loops back to block 47.

FIGS. 6A, 6B, 7 and 8 show an energy harvester 60A according to another embodiment of the invention. In many respects, energy harvester 60A is similar to energy harvester 60 described above and similar reference numerals are used to describe features of energy harvester 60A that are similar to corresponding features of energy harvester 60. Like energy harvester 60, energy harvester 60A is connected to knee 62 of the host by connection 100. Energy harvester 60A is configured to harvest energy associated with extension of knee 62 only. In addition, as discussed further below, energy harvester 60A is configurable to selectively harvest energy under mutualistic conditions when the knee flexor muscles are operating in negative mechanical power mode to decelerate the extension motion of knee 62.

Figures 6A, 6B:
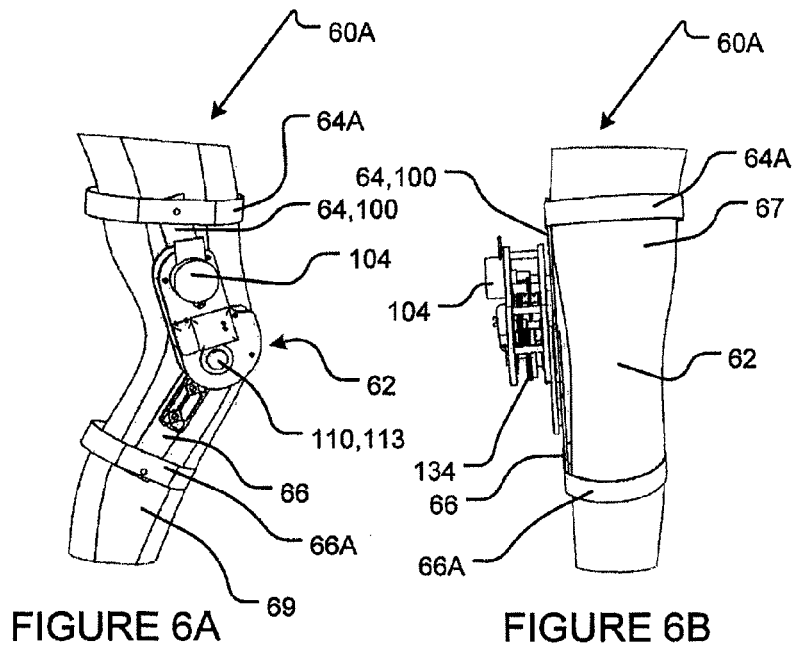
FIGS. 6A and 6B are respectively side and front views of an energy harvesting apparatus according to another embodiment of the invention.
Figure 7:
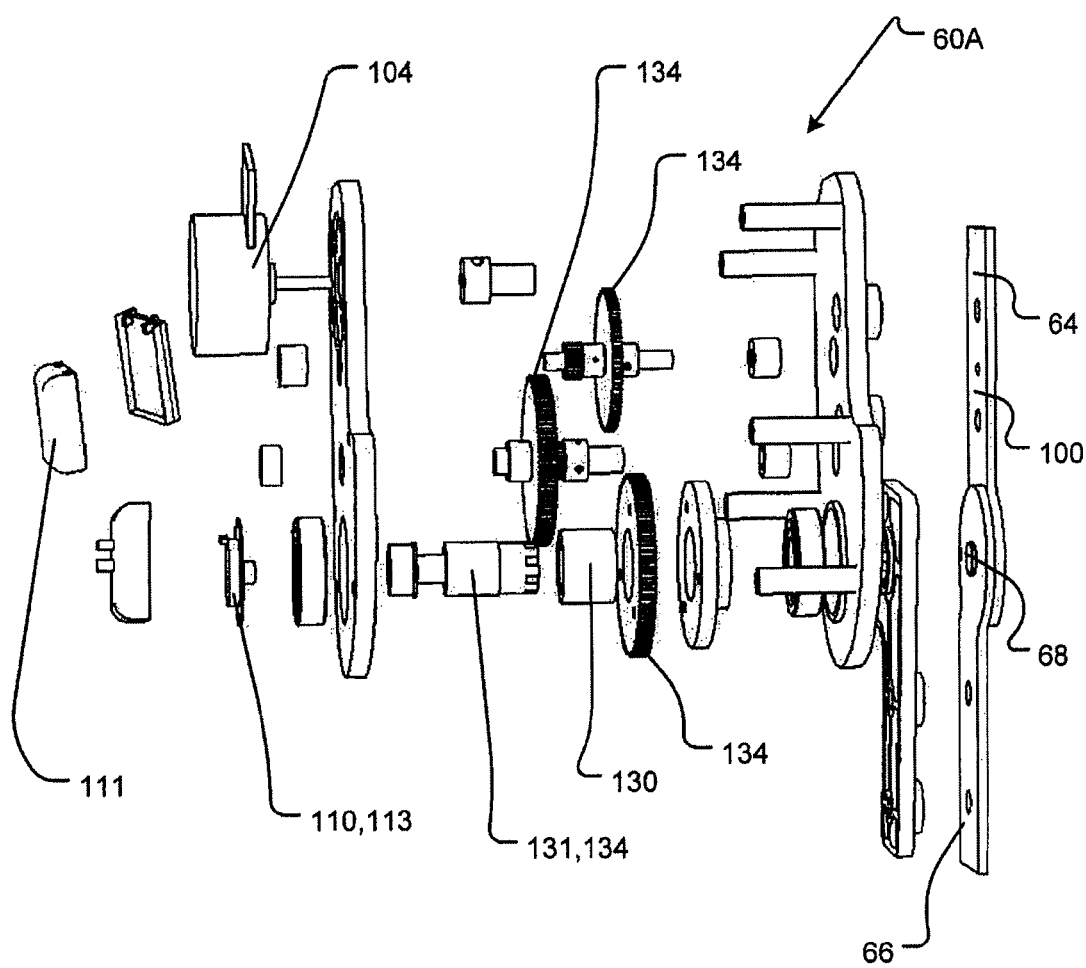
FIG. 7 is a partial exploded view of the FIG. 6A-6B energy harvesting apparatus.

Energy harvester 60A comprises a connection 100 which transfers mechanical power 112 from knee 62 to transmission 102. As shown in FIGS. 6A, 6B and 7, connection 100 of energy harvester 60A comprises an upper component 64 located above knee 62 and a lower component located below knee 62 which are coupled to one another by a pivot joint 68 that is generally coaxial with knee joint 62. In the illustrated embodiment, connection 100 also comprises upper band 64A which couples upper component 64 to thigh 67 of the host and lower band 66A which couples lower component 66 to calf 69 of the host. Upper band 64A and lower band 66A may be provided by a single component similar to a orthopedic knee brace, for example. The positions of upper band 64A and lower band 66A may be adjusted upwardly and downwardly (i.e. toward and/or away from knee joint 62) to adjust the coupling between the host and energy harvester 60A. Preferably, connection 100 is designed to have a minimal impact on the available range of motion of knee joint 62.

Figure 8:
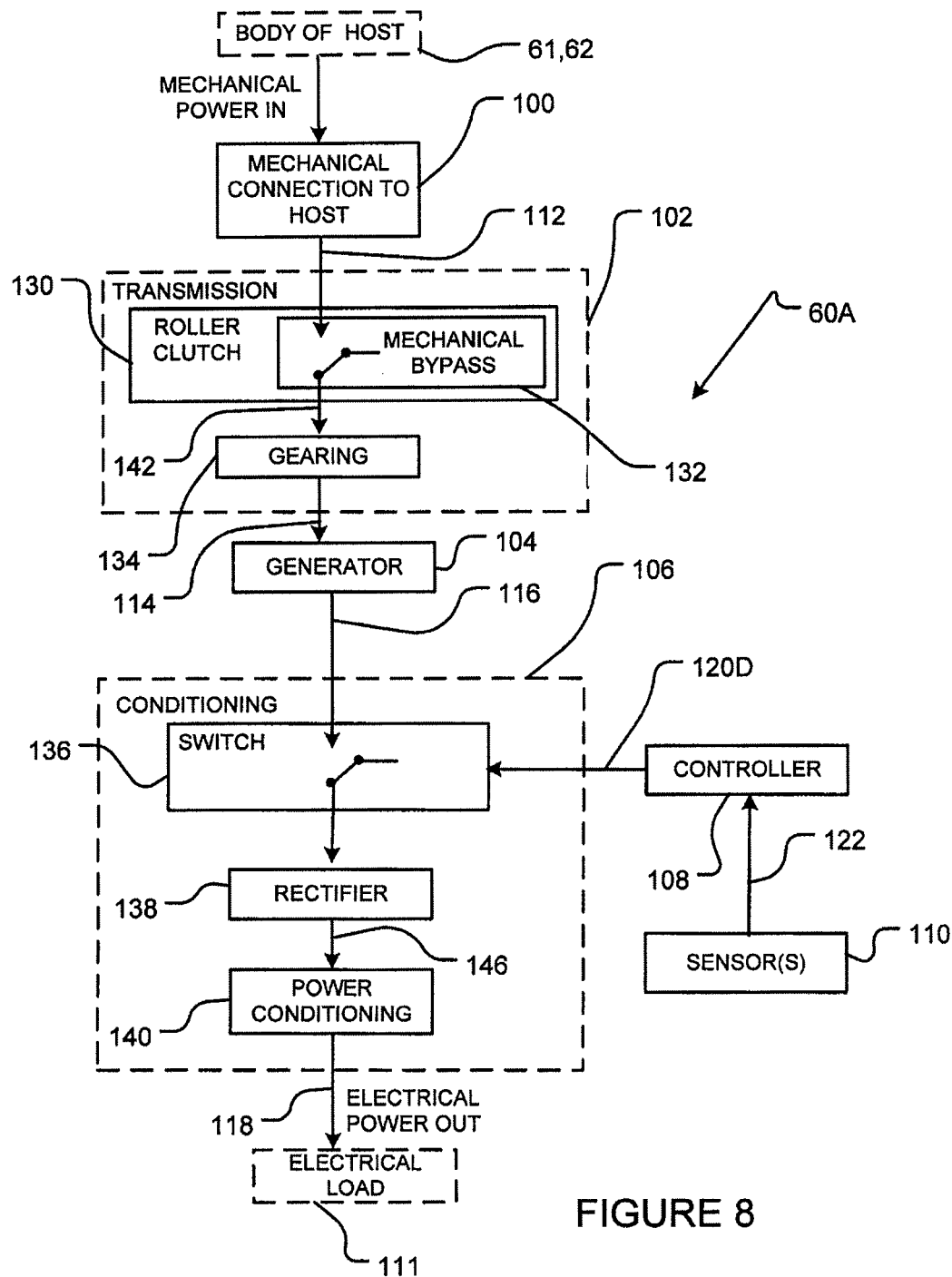
FIG. 8 is a schematic block diagram of the FIG. 6A-6B energy harvesting apparatus.

In the illustrated embodiment, connection 100 comprises a torque transfer shaft 131, such that movement of pivot joint 68 in either direction causes corresponding movement of shaft 131. Rotation of torque transfer shaft 131 is schematically represented in FIG. 8 by line 112.

Transmission 102 of energy harvester 60A converts relatively high-torque, low-speed mechanical power 112 (e.g. the type of mechanical power produced by knee joint 62 (see torque plot 26 of FIG. 2)) into relatively low-torque, high-speed mechanical power 114 which is suitable for use by generator 104. In the illustrated embodiment, transmission 102 of energy harvester 60A comprises a roller clutch 130 and a gear train 134.

As discussed above, energy harvester 60A only harvests energy associated with the extension of knee joint 62. This functionality is provided by roller clutch 130 which comprises a mechanical bypass 132. Roller clutch 130 is a unidirectional torque transfer mechanism. When shaft 131 rotates in a particular direction corresponding, in this embodiment, to extension of knee joint 62, roller clutch 130 engages shaft 131, thereby causing rotation of roller clutch 130 and corresponding rotation of gearing 134. Conversely, when shaft 131 rotates in the opposing direction corresponding, in this embodiment, to flexion of knee joint 62, mechanical bypass 132 allows shaft 131 to rotate freely relative to roller clutch 130. The intermittent rotation of roller clutch 130 (corresponding to extension of knee joint 62) causes corresponding intermittent rotation of gearing 134 with relatively high-torque and relatively low-speed. The intermittent rotation of roller clutch 130 is represented in FIG. 8 by line 142.

The intermittent rotation of shaft 131 (mechanical power 142) is transferred to gearing mechanism 134. Gearing mechanism 134 has a relatively high input to output gear ratio, so that relatively high-torque, low-speed mechanical power 142 is converted to relatively high-speed, low-torque mechanical power (represented in FIG. 8 by line 114). In particular embodiments, the input to output gearing ratio of gearing mechanism 134 may be in a range of 25-500. Relatively high-speed, low-torque mechanical power 114 output by gearing mechanism 134 is preferably configured (by gearing mechanism 134) to provide mechanical power suitable for input to generator 104. Gearing mechanism 134 is preferably relatively lightweight and not overly cumbersome. In other embodiments, the torque/speed conversion function of gearing mechanism 134 is implemented by other transmission systems and combinations of transmission systems, such as belt and pulley-based transmission systems, rack and pinion-based transmission systems and the like, for example.

Mechanical power 114 is received by generator 104. In general, generator 104 can comprise any suitable generator capable of converting mechanical power 114 into electrical power 116. Preferably, generator 104 is relatively lightweight and is not overly cumbersome. In one particular embodiment, generator 104 comprises a rotary-magnetic brushless DC motor which outputs three phase electrical output power 116. Those skilled in the art will appreciate that there are a relatively large variety of generators capable of converting mechanical power 114 into electrical power 116. In general, generator 104 may comprise any suitably configured generator.

In the illustrated embodiment, energy harvester 60A comprises a signal conditioner 106. Signal conditioner 106 functions generally to condition electrical power signal 116 output from generator 104 to a form suitable for use by electrical load 111. Accordingly, signal conditioner 106 may take a wide variety of forms and may comprise a wide variety of components, depending on the particulars of generator 104 (and its output power signal 116) and depending on the nature of electrical load 111 and its input requirements.

In the illustrated embodiment, generator 104 comprises a rotary-magnetic brushless DC motor which outputs a three phase electrical power signal 116 and electrical load 111 comprises a rechargeable DC battery which requires a single-phase electrical input signal 118. In the illustrated embodiment, to provide this multi-phase to single-phase conversion, signal conditioner 106 comprises a full wave rectifier 138 and associated power conditioning circuitry 140. Power conditioning circuitry 140 may comprise one or more filters to reduce the ripple voltage of signal 146 output from rectifier 138 before providing electrical power output 118 to electrical load 111.

In the illustrated embodiment, signal conditioner 106 also comprises a switch 136, which is controlled by signal 120D from controller 108. When switch 136 is closed, electrical power signal 116 from generator 104 is transmitted to rectifier 138. However, when switch 136 is open, generator 104 is open circuited such that electrical power signal 116 does not reach rectifier 138. In this manner, when switch 136 is open, electrical load 111 is decoupled from the motion of knee 62 and the resistance to knee motion is reduced. Switch 136 may generally comprise any switch that is controllable by signal 120D (e.g. solid state switches, electro-mechanical switches or the like). In one particular embodiment, switch 136 comprises the AQZ202 switch manufactured by Panasonic Corporation.

As discussed above, energy harvester 60A is configurable such that it harvests energy under mutualistic conditions. To achieve this objective, controller 108 uses feedback signal 122 from sensor(s) 110 to determine whether or not conditions are suitable for mutualistic energy harvesting. When controller 108 determines that conditions are suitable for mutualistic energy harvesting, controller 108 sends a signal 120D which causes switch 136 to be closed and electrical signal 116 from generator 104 to be received by rectifier 138. Conversely, when controller 108 determines that conditions are not suitable for mutualistic energy harvesting, controller 108 sends a signal 120D which causes switch 136 to open, thereby decoupling electrical load 111 from the motion of knee 62.

In this manner, controller 108 uses signal 120D to control switch 136 thereby causing energy harvester 60A to selectively harvest energy under mutualistic conditions.

In the illustrated embodiment, switch 136 represents a means for selectively coupling the movement of knee 62 to, and decoupling the movement of knee 62 from, electrical load 111 in response to a signal from controller 108. As discussed above in relation to energy harvester 60, energy harvester 60A may additionally or alternatively comprise a number of different means for selectively coupling the movement of knee 62 to, and decoupling the movement of knee 62 from, electrical load 111 in response to a signal from controller 108. Such means may comprise electrical means, mechanical means and/or electro-mechanical means and such means may be located at various places within energy harvester 60A.

To selectively harvest energy under mutualistic conditions, controller 108 uses feedback signal 122 from sensor(s) 110 to make a decision about whether or not current operating conditions are mutualistic. In one particular embodiment, controller 108 is configured to implement model-based control. For example, when knee 62 is being used in a repetitive manner (e.g. when walking, running or performing knee bends), the movement of knee 62 can be predicted relatively accurately based on a model. Such a model may comprise a known model corresponding to the repetitive movement (e.g. a known model relating to human walking patterns or human knee bend patterns or human cycling patterns). Such a model may be constructed from previous measurements on the host or on one or more other subjects, for example. Those skilled in the art will appreciate that there are a number of ways in which suitable models could be constructed. Controller 108 can be programmed or otherwise configured with information relating to one or more models and can use such model(s) in conjunction with feedback signal 122 from sensor(s) 110 to predict whether or not current operating conditions are mutualistic.

In the illustrated embodiment of FIGS. 6A, 6B, 7 and 8, controller 108 of energy harvester 60A makes use of such model-based control to determine when conditions are mutualistic. As discussed above, energy harvester 60A is configured to harvest energy associated with the movement of knee 62 in the extension direction only. When the host is walking, plots 24, 26, 28 and 32 (FIG. 2) show that region 28B represents a time where: (i) knee 62 is extending (indicated by an angular velocity (plot 24) greater than zero); and (ii) the knee flexor muscles are operating in a negative mechanical power mode to decelerate the extension motion of knee 62 (i.e. conditions are mutualistic—indicated by plot 28 being less than zero and plot 32 showing a high level of activity of the knee flexor muscles and also indicated by torque (plot 26) and angular velocity (plot 24) having opposite signs). Accordingly, region 28B represents an ideal time for energy harvester 60A to harvest energy. When energy harvester 60A harvests energy in region 28B, the mechanical power required to turn generator 104 actually assists the knee flexor muscles to decelerate the extension of knee 62 (i.e. reducing the effort and/or metabolic cost associated with decelerating the extension of knee 62).

As discussed above, controller 108 makes use of feedback signal 122 to help make the decision as to whether conditions are mutualistic. In the illustrated embodiment of FIGS. 6A, 6B, 7 and 8, sensor(s) 110 of energy harvester 60A comprise a potentiometer 113, which produces a feedback signal 122 representative of the angular position of knee 62. It will be appreciated by those skilled in the art that other types of sensors could be used to provide this angular position feedback signal 122 or similar information about the angular characteristics of knee 62. Such other types of sensors may include optical encoders, magnetic encoders, mechanical encoders, accelerometers and/or rate gyroscopes for example.

Figure 9:
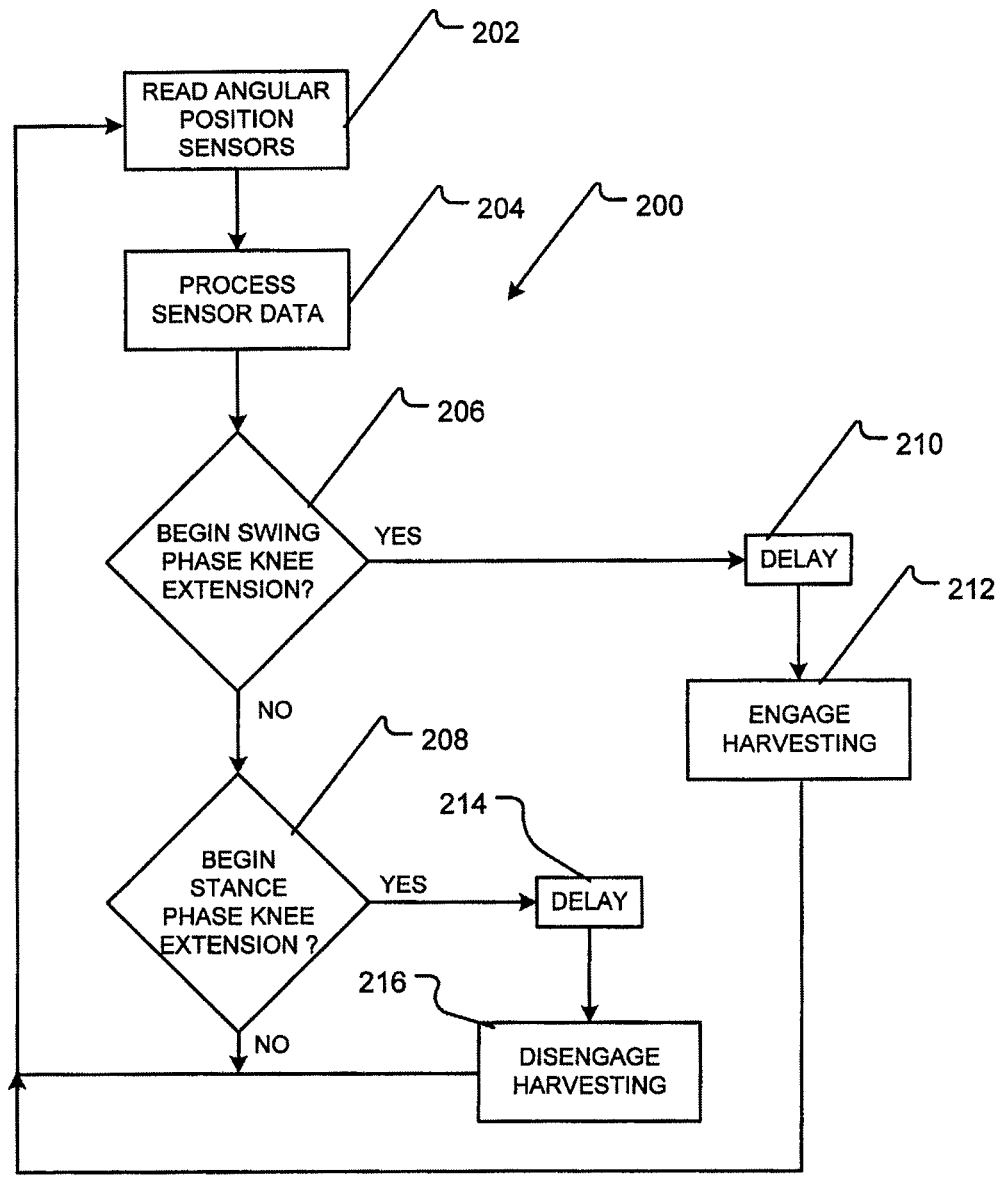
FIG. 9 is a schematic block diagram showing a method for determining when to engage the FIG. 6A-6B energy harvesting apparatus to harvest energy under mutualistic conditions according to a particular embodiment of the invention.
Figure 10:
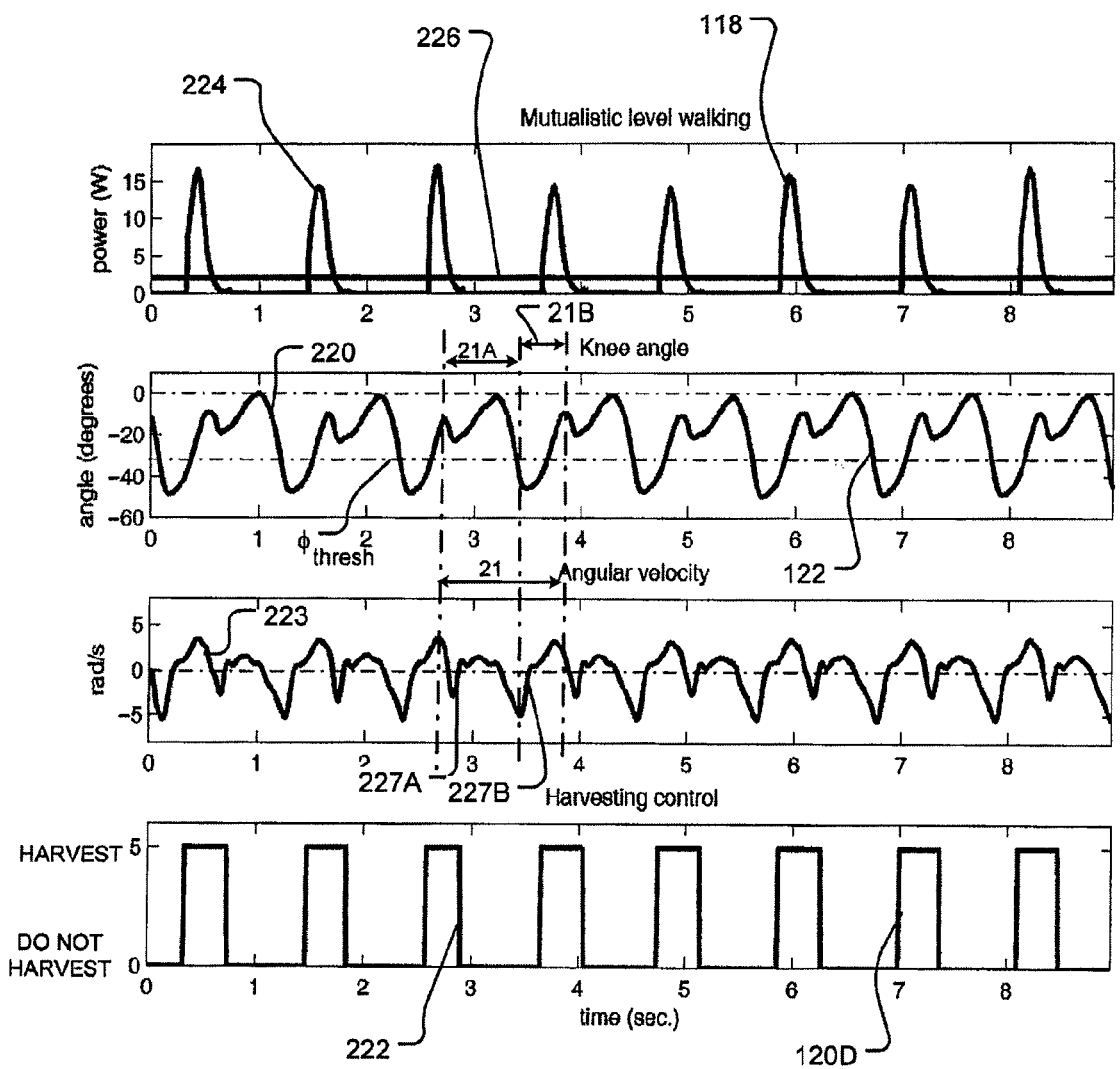
FIG. 10 shows a number of plots relating to the harvesting of energy while the host is walking using the FIG. 6A-6B energy harvesting apparatus in accordance with the method of FIG. 9.

FIG. 9 is a block diagram illustrating a method 200 for predicting the existence of mutualistic conditions and for harvesting energy during such mutualistic conditions and disengaging energy harvesting when conditions are non-mutualistic. Method 200 is suitable for use with energy harvester 60A of FIGS. 6A, 6B, 7 and 8. Those skilled in the art will appreciate, however, that method 200 may be modified for use with other embodiments. FIG. 10 shows a number of plots relating to the harvesting of energy while the host is walking using energy harvester 60A in accordance with method 200. Characteristics of the FIG. 10 plots (e.g. the amplitude and frequency) may vary for each individual host and for the conditions being experienced by a particular host.

As discussed above, walking is a relatively repetitive motion. Plot 220 shows the angle of knee joint 62 of a particular host during a walking motion. As discussed above, controller 108 may determine the angle of knee joint 62 using feedback signal 122 from sensor(s) 110 (i.e. potentiometer 113 in the illustrated embodiment). When the host is walking, each cycle 21 of plot 220 comprises a stance phase 21A and a swing phase 21B. Plot 223 shows the angular velocity of knee joint 62. The angular velocity plot 223 may be obtained by taking the derivative of the angular position plot 220, for example.

Method 200 of FIG. 9 makes use of model-based control. In the illustrated embodiment, method 200 also makes use of sensor(s) which provide information relating to the angular position or other angular characteristics of knee 62. In alternative embodiments, method 200 may make use of other sensors that detect one or more characteristics associated with a repetitive motion (e.g. walking). By way of non-limiting example, such other sensors may comprise pressure sensors, which detect heel strike.

Method 200 begins in block 202, where controller 108 reads feedback signal 122 from angular position sensors 110. In block 204, controller 108 processes the newly acquired sensor information. The block 204 processing may comprise filtering, scaling, offsetting or otherwise digitally manipulating the incoming angular position data, for example. In some embodiments, some of the block 204 processing may occur in the analog domain. In the particular embodiment of method 200, block 204 comprises taking a derivative of the incoming angular position data to obtain data representative of the angular velocity.

Block 206 involves an inquiry into whether the processed sensor data indicates that knee 62 has just begun the swing phase knee extension. The swing phase knee extension is shown as region 22E of plot 22 (FIG. 2). In one particular embodiment, the block 206 inquiry involves an inquiry into whether:
  (i) the angular velocity crosses zero from a negative value to a positive value (i.e. the angular velocity crosses zero with a positive slope); and
  (ii) the angular position is lower than a threshold value ($\phi_{thresh}$).

An angular velocity zero crossing with a positive slope is indicative of a transition from flexion toward extension. However, as shown in FIG. 10, within each walking cycle 21, there are two such transitions 227A and 227B, where the angular velocity exhibits a zero crossing with a positive slope. The angular position being lower than a threshold value ($\phi_{thresh}$) can be used to indicate that the particular positive-sloped zero crossing of the angular velocity being detected represents the beginning of the swing phase knee extension. As shown in FIG. 10, the positive-sloped angular velocity zero crossing associated with transition 227A has an associated angular position greater than the threshold value ($\phi_{thresh}$), meaning that the positive-sloped angular velocity zero crossing associated with transition 227A does not correspond with the swing phase knee extension. On the other hand, the positive-sloped angular velocity zero crossing associated with transition 227B has an associated angular position that is less than the threshold value ($\phi_{thresh}$), meaning that the positive-sloped angular velocity zero crossing associated with transition 227B represents the beginning of the swing phase knee extension.

Those skilled in the art will appreciate that there are other techniques which may be used to predict the beginning of the swing phase knee extension in block 206. For example, it is not strictly necessary to detect that the angular velocity zero crossing has a positive slope. In the illustrated example associated with walking (FIG. 10), controller 108 may conclude that the beginning of the swing phase knee extension occurs whenever the angular velocity crosses zero and the angular position is less than the threshold value ($\phi_{thresh}$). In other embodiments, controller 108 may make use of acceleration data (i.e. by taking a second derivative of the angular position data or by directly detecting acceleration data) to assist with determining the beginning of the swing phase knee extension. It will be appreciated by those skilled in the art, that zero acceleration represents the transition from stance phase 21A to swing phase 21B (FIG. 10). In still other embodiments, sensors may be provided to detect other characteristics associated with repetitive motion and such other characteristics may be used to assist with determining the beginning of the swing phase knee extension. By way of non-limiting example, a pressure sensor placed on the foot may be used to detect the transition from stance phase 21A to swing phase 21B. If the start of the swing phase is known (e.g. using an accelerometer or a foot pressure sensor), a delay may be used as a basis for predicting the start of the swing phase knee extension. Such a delay may be based on the frequency of the repetitive motion, for example.

If the block 206 inquiry indicates that the swing phase knee extension has just begun (block 206 YES output), then method 200 proceeds to block 210 where a short delay occurs before method 200 proceeds to block 212. The amount of the block 210 delay may be constant or variable. The block 210 delay may be separately configured (or configurable) for each user. The block 210 delay may be related to the period of the walking cycle 21 of a particular host or to the slope of the terrain. The block 210 delay may be adaptive. By way of non-limiting example, if the period of the walking cycle changes or the slope of the terrain changes, then the block 210 delay may change accordingly. The block 210 delay may be configured to achieve improved performance (e.g. greater power output and/or improved user comfort). In some cases, the block 210 delay can be set to zero. In block 212, controller 108 outputs signal 120D which causes switch 136 to enter its closed state, where generator 104 is coupled to electrical load 111 and energy harvesting commences. Method 200 then loops back to block 202, where controller 108 obtains more angular position data from sensors 110.

Plot 222 of FIG. 10 represents control signal 120D which, in the illustrated embodiment, is a binary signal having an enable harvest level and a disable harvest level. Block 212 corresponds to a transition of control signal 120D from its disable harvest level to its enable harvest level. In response to this transition of control signal 120D, switch 136 is closed and the motion of knee 62 is coupled to electrical load 111, such that electrical power output signal 118 is delivered to load 111.

The next time method 200 arrives at block 206, the swing phase knee extension will have begun on the previous loop, so method 200 will exit block 206 through the block 206 NO output into block 208. In general, block 208 involves determining whether the energy harvesting engaged in block 212 should be discontinued (e.g. because conditions are no longer mutualistic). If energy harvesting is engaged at (or near) the beginning of the swing phase knee extension region 22E of plot 22 (FIG. 2), then it should be discontinued prior to the commencement of stance phase knee extension region 22B of plot 22 (FIG. 2). Even if switch 136 is closed, energy harvesting will not occur in region 22A of plot 22 (FIG. 2), as knee 62 is flexing and roller clutch 130 acts to decouple knee 62 from generator 104. Accordingly, in the illustrated embodiment, the block 208 inquiry into whether the energy harvesting engaged in block 212 should be discontinued comprises an inquiry into whether the processed sensor data indicates that knee 62 has just begun the stance phase knee extension.

As shown in FIG. 10, commencement of the stance phase knee extension corresponds with the positive-sloped angular velocity zero crossing associated with transition 227A. In one particular embodiment, the block 208 inquiry involves an inquiry into whether:
  (i) the angular velocity crosses zero from a negative value to a positive value (i.e. the angular velocity crosses zero with a positive slope); and
  (ii) the angular position is greater than the threshold level ($\phi_{thresh}$).

Those skilled in the art will appreciate that there are other techniques which may be used to predict the beginning of the stance phase knee extension in block 208. For example, it is not strictly necessary to detect that the angular velocity zero crossing has a positive slope. In the illustrated example associated with walking (FIG. 10), controller 108 may conclude that the beginning of the stance phase knee extension occurs whenever the angular velocity crosses zero and the angular position is greater than the threshold value ($\phi_{thresh}$). In other embodiments, controller 108 may make use of acceleration data (i.e. by taking a second derivative of the angular position data or by directly detecting acceleration data) to assist with determining the beginning of the swing phase knee extension. It will be appreciated by those skilled in the art, that zero acceleration represents a minimum of the angular velocity that precedes the stance phase knee extension (see FIGS. 2 and 10). In still other embodiments, sensors may be provided to detect other characteristics associated with repetitive motion and such other characteristics may be used to assist with determining the beginning of the swing phase knee extension. By way of non-limiting example, a pressure sensor placed on the foot may be used to detect the transition from swing phase 21B to stance phase 21A. If either of these conditions (e.g. the angular velocity minimum that precedes the stance phase knee extension or the beginning of the stance phase), a delay may be used as a basis for predicting the start of the stance phase knee extension. Such a delay may be based on the frequency of the repetitive motion, for example.

If the block 208 inquiry indicates that stance phase knee extension has not just begun (block 208 NO output) and switch 136 is closed (i.e. energy harvester 60A is harvesting energy), then switch 136 remains closed and energy harvester 60A continues to harvest energy while method 200 loops back to block 202. If on the other hand, the block 208 inquiry indicates that the stance phase knee extension has just begun (block 208 YES output) and switch 136 is closed (i.e. energy harvester 60A is harvesting energy), then method 200 proceeds to block 214 where a short delay occurs before method 200 proceeds to block 216. The amount of the block 214 delay may be constant or variable. The block 214 delay may be separately configured (or configurable) for each user. The block 214 delay may be related to the period of the walking cycle 21 of a particular host or the slope of the terrain on which the host is walking. The block 214 delay may be adaptive. By way of non-limiting example, if the period of the walking cycle or the slope of the terrain changes, then the block 214 delay may change accordingly. The block 214 delay may be configured to achieve improved performance (e.g. greater power output and/or improved user comfort). In some cases, the block 214 delay can be set to zero.

In block 216, controller 108 outputs signal 120D which causes switch 136 to enter its open state, where generator 104 is decoupled from electrical load 111 and energy harvesting is discontinued. Block 216 comprises a transition of control signal 120D (plot 222 of FIG. 10) from its enable harvest level to its disable harvest level. In response to this transition of control signal 120D, switch 136 is opened and the motion of knee 62 is decoupled from electrical load 111. After block 216, method 200 again loops back to block 202.

If the block 208 inquiry indicates that stance phase knee extension has not just begun (block 208 NO output) and switch 136 is open (i.e. energy harvester 60A is not harvesting energy), then method 200 loops back to block 202 without changing the status of switch 136.

Plot 224 represents the instantaneous power of electrical power output signal 118. It can be seen by comparing plot 224 and plot 222 that electrical power is only harvested when control signal 120D (plot 220) is at its enable harvest level. As discussed above, control signal 120D is at its enable harvest level during the swing phase knee extension, when the knee flexor muscles are acting in a negative mechanical power mode to decelerate the extension of knee 62 and conditions are mutualistic. Plot 226 represents the average power of electrical power output signal 118 (i.e. the average of plot 224). In the particular example shown in FIG. 10, harvester 60A generates an average power of 2.4 W when the host is walking.

In other embodiments, model-based control similar to that of FIGS. 9 and 10 may be used for other cyclical movements. Non-limiting examples of such cyclical movements include: running, jumping, knee bends, climbing, ascending and/or descending stairs or embankments, and the like.

In another embodiment, controller 108 is configured to directly sense muscle activity to help determine when conditions are mutualistic. In such muscle activity-based control, sensors 110 may comprise one or more position sensors for sensing the angle of a joint or other angular characteristics (e.g. angular velocity or acceleration) of a joint (e.g. knee 62) and one or more sensors for sensing activity within one or more muscles (e.g. knee flexors). Any of the aforementioned sensors could be used to determine the angular characteristic (s) of the joint. Suitable muscle activity sensors include electromyography (EMG) sensors. When muscle activity-based control is used for the particular energy harvester 60A of FIGS. 6A, 6B, 7 and 8 and energy is harvested from movement of knee 62 in the extension direction only, feedback signal 122 will contain information relating to the angular characteristic(s), such as position, of knee 62 and muscle activity sensors will be configured (e.g. located) to sense the activity of the knee flexor muscles.

Figure 11:
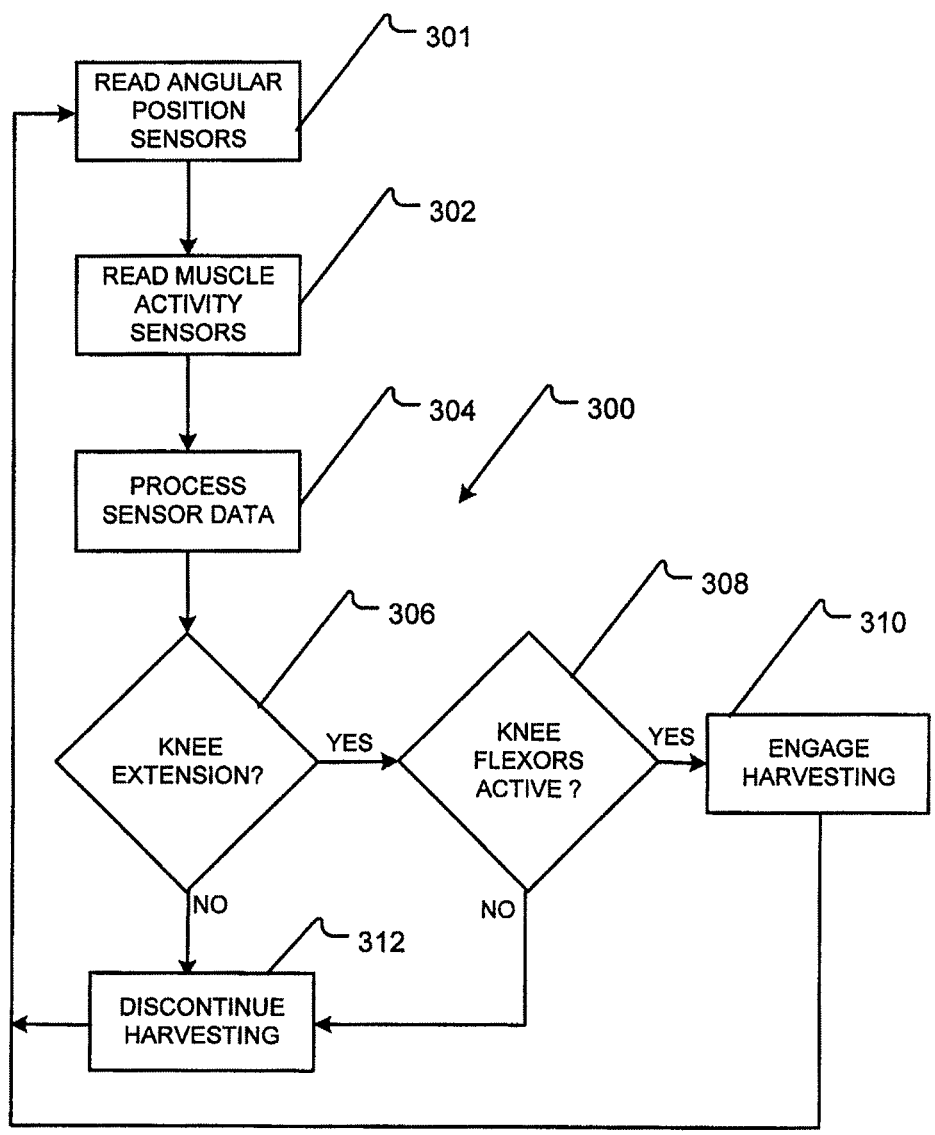
FIG. 11 is a schematic block diagram showing a method for determining when to engage the FIG. 6A-6B energy harvesting apparatus to harvest energy under mutualistic conditions according to another embodiment of the invention.

FIG. 11 is a block diagram depicting a method 300 for predicting the existence of mutualistic conditions using muscle activity-based control. Method 300 is suitable for use with energy harvester 60A of FIGS. 6A, 6B, 7 and 8 but may be generalized for use with other embodiments. Method 300 makes use of one or more position sensor(s) which provide information relating to the angular position of knee 62 and one or more muscle activity sensor(s) which provide information relating to the activity of the knee flexor muscles. Method 300 begins in block 301, where controller 108 reads feedback signal 122 from angular position sensor(s) 110. Method 300 then proceeds to block 302, where controller reads feedback signal 122 from muscle activity sensor(s) 110. In block 304, controller 108 processes the newly acquired sensor information. The block 304 processing may comprise filtering, scaling, offsetting or otherwise digitally manipulating the incoming data, for example. In some embodiments, some of the block 304 processing may occur in the analog domain (i.e. prior to the block 301 and/or 302 data acquisition). In this particular embodiment, block 304 comprises taking a derivative of the incoming angular position data to obtain data representative of the angular velocity. In this particular embodiment, block 304 comprises rectifying and filtering the muscle activity data.

Method 300 then proceeds to block 306 which involves an inquiry as to whether knee 62 is extending. The block 306 inquiry may comprise comparing the time derivative of the angular position data (i.e. the angular velocity) to zero. If the angular velocity is greater than zero, then knee 62 is extending and if the angular velocity is less than zero, then knee 62 is flexing. Alternatively, the block 306 inquiry may involve looking at historical angular position data to determine if the current angular position is greater than the previous angular position (in which case knee 62 is extending) or if the current angular position is less than the previous angular position (in which case knee 62 is flexing).

If the block 306 inquiry indicates that knee 62 is flexing (block 306 NO output), then method 300 proceeds to block 312, where harvesting is disabled before looping back to block 301 to collect more data. If on the other hand the block 306 inquiry indicates that knee 62 is extending (block 306 YES output), then method 300 proceeds to block 308. Block 308 involves an inquiry into whether the knee flexor muscles are active. Block 308 may involve an inquiry into whether the activity level of the knee flexor muscles is above a certain threshold (see $I_{thresh}$ in EMG plot 32 of FIG. 2). If the block 308 inquiry indicates that there is insufficient activity in the knee flexor muscles (block 308 NO output), then method 300 proceeds to block 312, where harvesting is disabled before looping back to block 301 to collect more data. If on the other hand the block 308 inquiry indicates that there is sufficient knee flexor activity (block 308 YES output), then method 300 proceeds to block 310.

If method 300 arrives at block 310, then knee 62 is extending (block 306 YES output) and the knee flexor muscles are active in trying to decelerate this knee extension (block 308 YES output). Accordingly, the knee flexor muscles are operating in a negative mechanical power mode and conditions are mutualistic. If method 300 arrives at block 310, then controller 108 engages harvesting by sending the appropriate control signal 120D to switch 136 which in turn couples the movement of knee 62 to electrical load 111. In some embodiments, method 300 may optionally involve delaying for a short period before engaging harvesting in block 310. The amount of such a delay may be constant or may be separately configured (or configurable) for each user. The delay may be related to the period of the walking cycle 21 of a particular host. The delay may be configured to achieve improved performance (e.g. greater power output and/or improved user comfort). Method 300 then loops back to block 301 to obtain more data.

Figure 12:
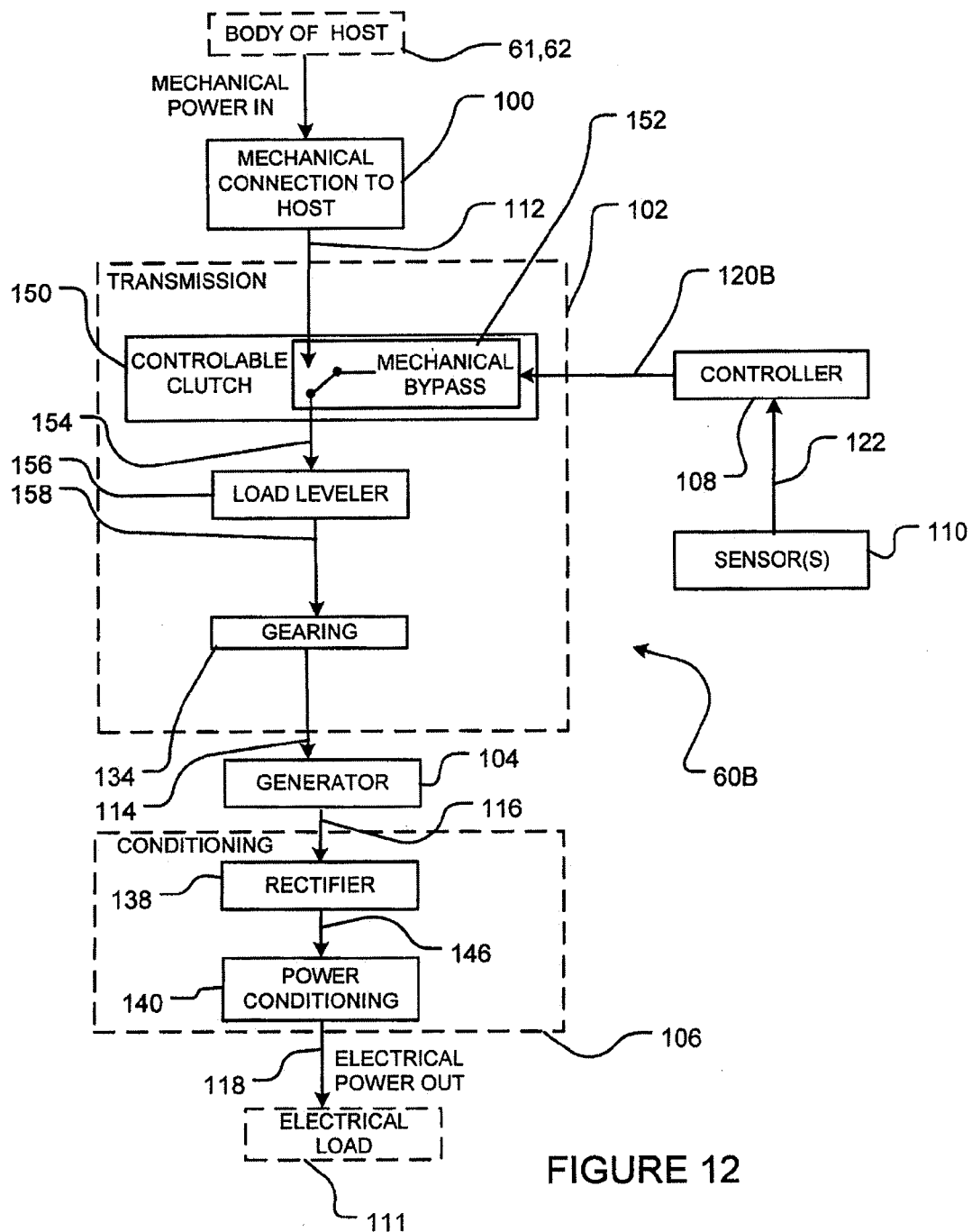
FIG. 12 is a schematic block diagram of an energy harvesting apparatus according to another embodiment of the invention.

FIG. 12 is a schematic block diagram of a energy harvesting apparatus 60B according to another embodiment of the invention. Energy harvesting apparatus 60B is similar in many respect to energy harvesting apparatus 60A and similar reference numerals are used to describe features of energy harvester 60B that are similar to corresponding features of energy harvester 60A.

Energy harvester 60B differs from energy harvester 60A in that rather than having an electronic switch 136 and a roller clutch 130, energy harvester 60B comprises a controllable clutch 150 which mechanically couples the movement of knee 62 to, and decouples the movement of knee 62 from, electrical load 111. Clutch 150 comprises a mechanical bypass 152 which is controlled by signal 120B from controller 108. When controller 108 decides that conditions are mutualistic and energy should be harvested, controller 108 causes control signal 120B to engage clutch 150 (i.e. to deactivate mechanical bypass 152) which in turn couples the movement of knee 62 to electrical load 111. When controller 108 decides that conditions are non-mutualistic or that energy should not otherwise be harvested (e.g. because knee 62 is flexing), controller 108 causes control signal 120B to disengage clutch 150 (i.e. to activate mechanical bypass 152) which in turn decouples the movement of knee 62 from electrical load 111.

The output of controllable clutch 150 (represented by line 154) is an intermittent and variable amplitude mechanical power. Energy harvester 60B also differs from energy harvester 60A in that energy harvester 60B comprises a load leveling mechanism 156, which receives intermittent and variable amplitude mechanical power 154 from clutch 150 and outputs relatively continuous mechanical power (represented by line 158). Relatively continuous mechanical power 158 is delivered to gearing 134 which outputs corresponding mechanical power 114 which may have a different speed and torque that mechanical power 158. Load leveling mechanism 156 is not necessary. However, load leveling mechanism 156 may improve the performance of energy harvesting apparatus 60B because generator 104 may exhibit better performance (i.e. better power conversion efficiency) when input mechanical power 114 is continuous rather than intermittent and variable.

In other respects, energy harvester 60B is similar to energy harvester 60A.

One advantage of energy harvester 60B over energy harvester 60A is that clutch 150 mechanically disengages gearing 134 and generator 104 from knee 62. Thus, when clutch 150 is disengaged and energy harvester 60B is not harvesting energy, the host does not have to move gearing 134 or generator 104. In contrast, energy harvester 60A requires that the host move gearing 134 and generator 104 when knee 62 is extending (i.e. roller clutch 130 is engaged) even if switch 136 is open and energy is not being harvested. When knee 62 is flexing, roller clutch 130 of energy harvester 60A provides benefits similar to those of clutch 150 of energy harvester 60B by mechanically disengaging gearing 134 and generator 104 from knee 62.

Energy harvesters 60A, 60B described above only harvest energy associated with the extension of knee 62. Those skilled in the art will appreciate that energy harvesters 60A, 60B could be modified to only harvest energy associated with the flexion of knee 62 when the energy harvesting conditions are primarily mutualistic. Such energy extraction conditions are exhibited, for example, in region 28A of plot 28.

Energy harvester 60A could be modified to harvest the energy associated with knee flexion by reconfiguring roller clutch 130 to engage gearing 134 when knee 62 is flexing and to disengage gearing 134 when knee 62 is extending (see FIG. 8). Energy harvester 60B does not require hardware modification to harvest energy during knee extension. Method 200 may be modified to harvest energy during knee flexion and when the energy harvesting conditions are primarily mutualistic by modifying block 206 and/or block 208 appropriately. By way of non-limiting example, the block 206 inquiry could be modified to consider whether stance phase 21A had just begun. It would not be necessary to change the block 208 inquiry. Such modification would allow controller 108 to use method 200 to engage energy harvesting during the time corresponding to region 28A and to disengage energy harvesting otherwise. Method 300 may be modified to harvest energy during knee flexion and when the energy harvesting conditions are primarily mutualistic by modifying the block 306 inquiry to consider whether knee 62 is flexing and by modifying the block 308 inquiry to consider whether the knee extensor muscles are active. Such modification would allow controller 108 to use method 300 to engage energy harvesting during the time corresponding to region 28A and to disengage energy harvesting otherwise.

Figure 13A:
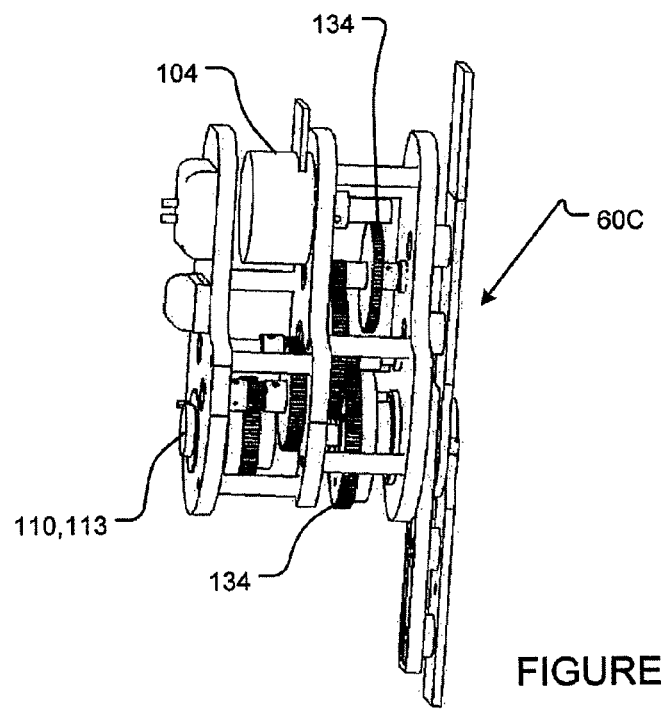
FIGS. 13A and 13B are respectively isometric and exploded isometric views of a bi-directional energy harvesting apparatus according to a particular embodiment of the invention.
Figure 13B:
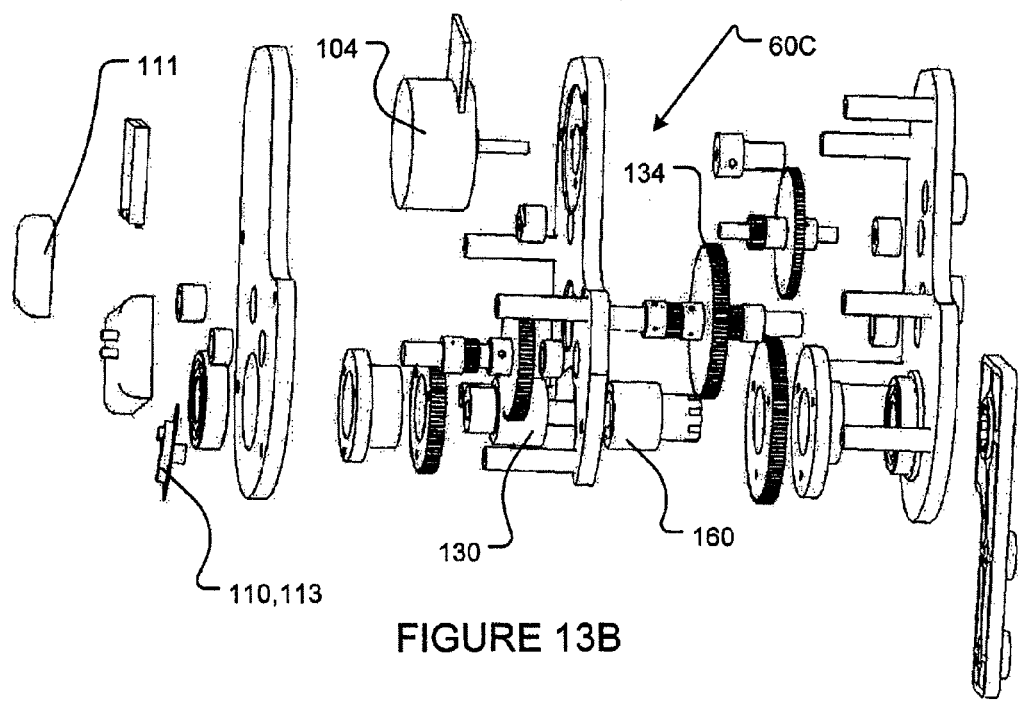
Figure 14:
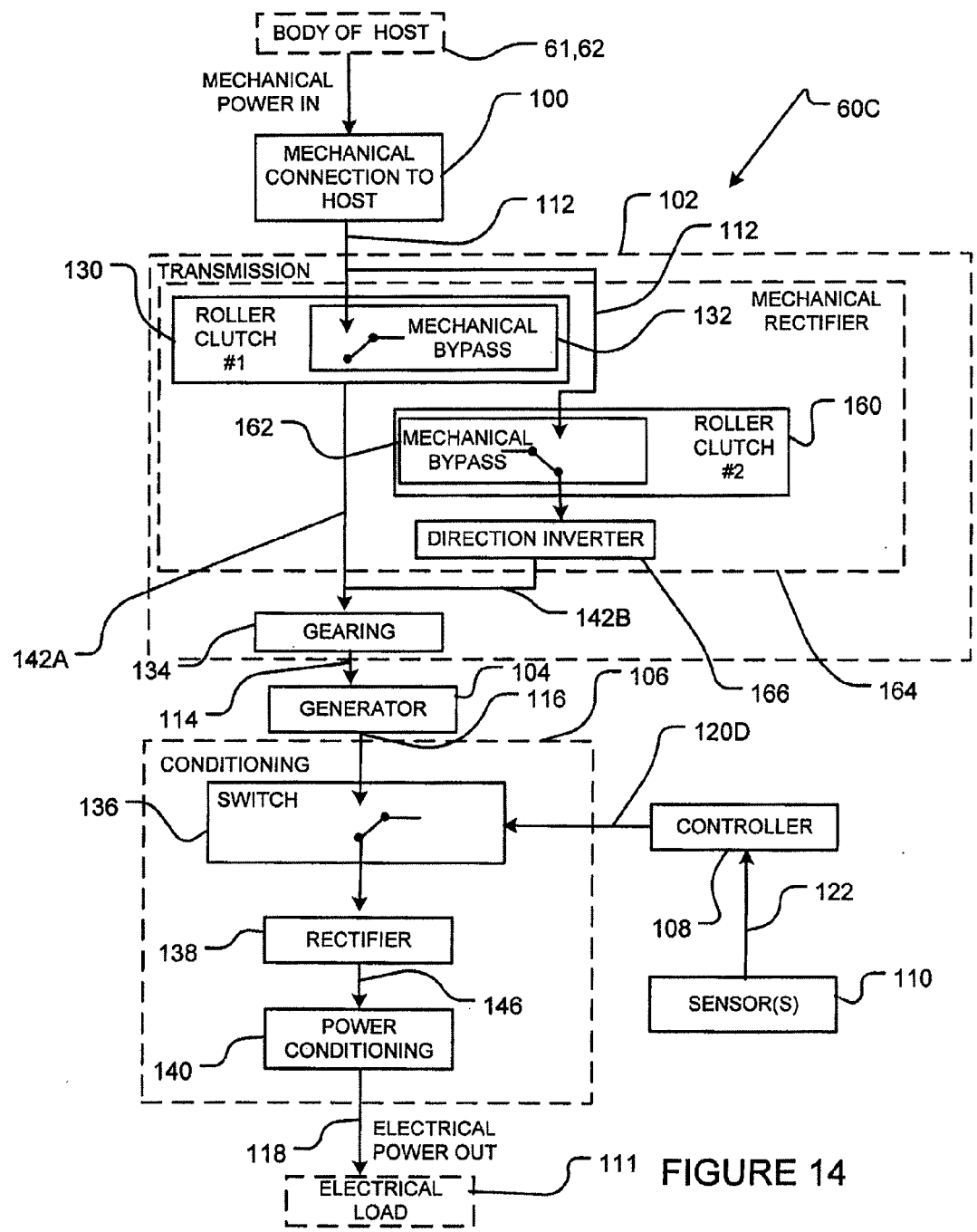
FIG. 14 is a schematic block diagram of the FIG. 13A-13B energy harvesting apparatus.

In some embodiments, energy may be harvested both when knee 62 is extending and when knee 62 is flexing. Energy harvesters which can harvest energy during extension and flexion may be said to be bi-directional. FIGS. 13A, 13B and 14 show a bi-directional energy harvesting apparatus 60C according to another embodiment of the invention. Energy harvester 60C is configured to harvest energy during knee flexion and during knee extension and primarily when the energy harvesting conditions are mutualistic. Energy harvesting apparatus 60C is similar in many respects to energy harvesting apparatus 60A and similar reference numerals are used to describe features of energy harvester 60C that are similar to corresponding features of energy harvester 60A.

Energy harvester 60C differs from energy harvester 60A in that energy harvester 60C comprises a mechanical rectifier 164 which converts both directions of motion of knee joint 62 (i.e. flexion and extension) into a single direction mechanical power signal. Mechanical rectifier 164 may comprise a pair of uni-directional torque transfer mechanisms 130, 160 configured in opposing directions with one of the torque transfer mechanisms coupled to a mechanical direction inverter 166. In the illustrated embodiment, torque transfer mechanisms 130, 160 comprise roller clutches 130, 160. Roller clutches 130, 160 are configured such that: (i) roller clutch 130 directly engages gearing 134 (as represented by line 142A) when knee 62 moves in the extension direction and disengages from gearing 134 (via mechanical bypass 132) when knee 62 moves in the flexion direction; and (ii) roller clutch 160 engages gearing 134 via direction inverter 166 (as represented by line 142B) when knee 62 moves in the flexion direction and disengages from gearing 134 (via mechanical bypass 162) when knee 62 moves in the extension direction. Because of direction inverter 166 (which acts when knee 162 is moving in the flexion direction and roller clutch 160 is engaged), movement of knee 162 in both the flexion direction and the extension direction cause movement of gearing 134 in the same direction. Direction inverter 166 may be implemented by coupling an additional gear between roller clutch 160 and gearing 134, for example. Those skilled in the art will appreciate that there are a variety of additional or alternative mechanisms that could be used to implement direction inverter 166.

In other respects, the components of energy harvester 60C are similar components of energy harvester 60A.

In contrast to energy harvester 60A, controller 108 may be configured to cause signal 120D to close switch 136 (i.e. coupling the motion of knee 62 to load 111) when: (i) knee 62 is extending and the energy harvesting conditions are determined by controller 108 to be primarily mutualistic; and/or (ii) knee 62 is flexing and the energy harvesting conditions are determined by controller 108 to be primarily mutualistic. Referring to FIG. 2, region 28B (of plot 28) exhibits mutualistic conditions in swing phase 21B, where knee 62 is extending and the knee flexor muscles are active to decelerate this extension, and region 28A exhibits mutualistic conditions in stance phase 21A, where knee 62 is flexing and the knee extensor muscles are active to decelerate this flexion.

Plot 28 (FIG. 2) also shows that there is a small region 28C exhibiting non-mutualistic conditions between mutualistic region 28B and an adjacent mutualistic region 28A. In theory, energy could be harvested in region 28B and region 28A only. However, in practice, for harvesting energy from a walking human, the inventors have determined that it is sometimes convenient to harvest energy from the onset of mutualistic region 28B, through mutualistic region 28B, non-mutualistic region 28C and subsequent mutualistic region 28A and to discontinue energy harvesting at the conclusion of mutualistic region 28A. Energy harvesting in region 28C is non-mutualistic. However, this non-mutualistic energy harvesting in region 28C is relatively insignificant in terms of its additional metabolic cost when compared to the metabolic power savings associated with mutualistic energy harvesting in regions 28A and 28B. In addition, energy harvesting in regions 28A, 28B and 28C reduces the frequency of engagement and disengagement of load 111 (which would occur if energy was harvested in regions 28A and 28B only) and avoids the possible negative impact of such rapid engagement and disengagement on the coordination of the host.

As with the extension only energy harvester 60A, controller 108 of energy harvester 60C may make the decision as to when to harvest energy using model-based control techniques or muscle activity-based control techniques so as to harvest energy under mutualistic conditions and to disengage energy harvesting during non-mutualistic conditions.

Figure 15:
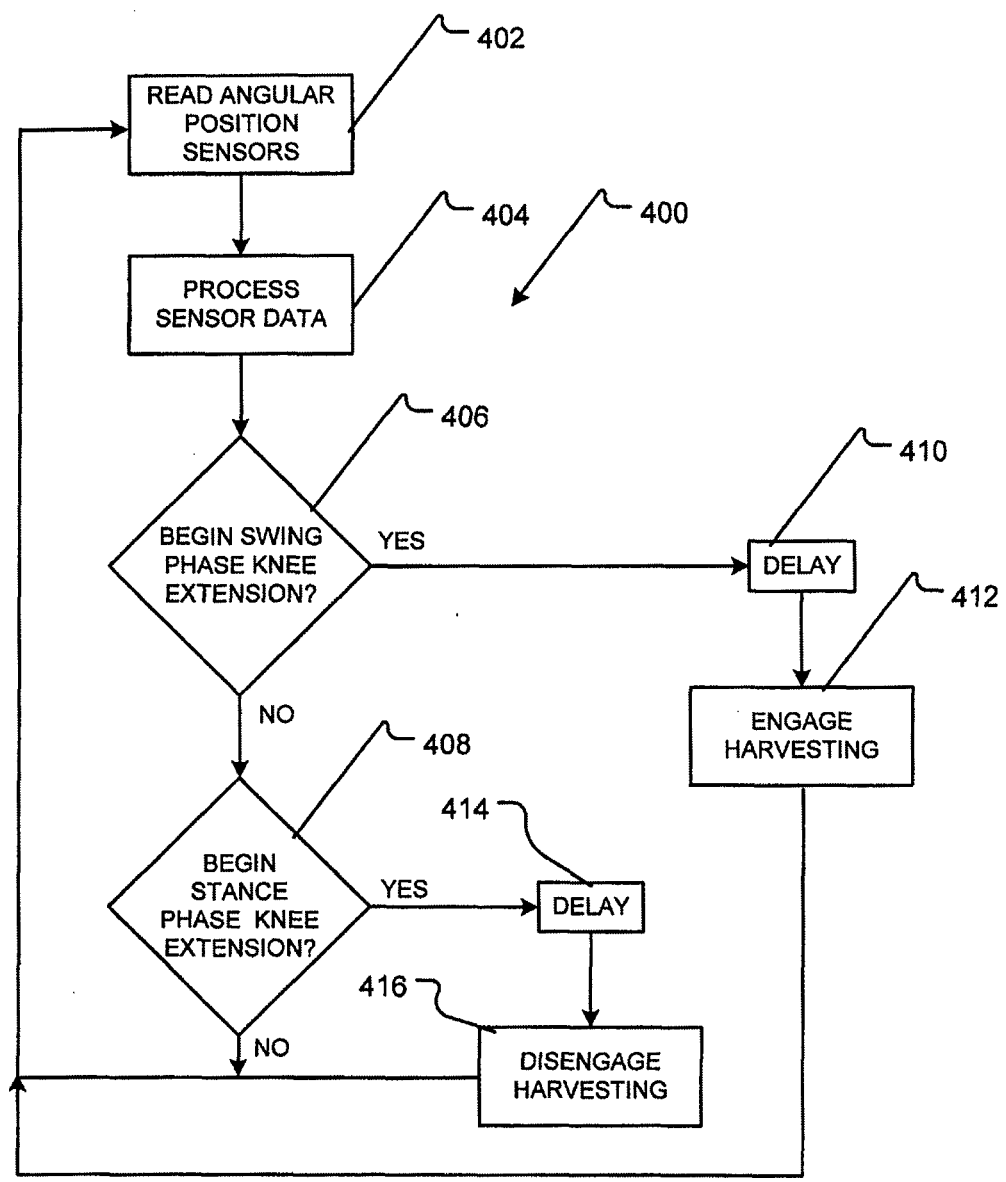
FIG. 15 is a schematic block diagram showing a method for determining when to selectively harvest energy using the FIG. 13A-13B energy harvesting apparatus according to a particular embodiment of the invention.
Figure 16:
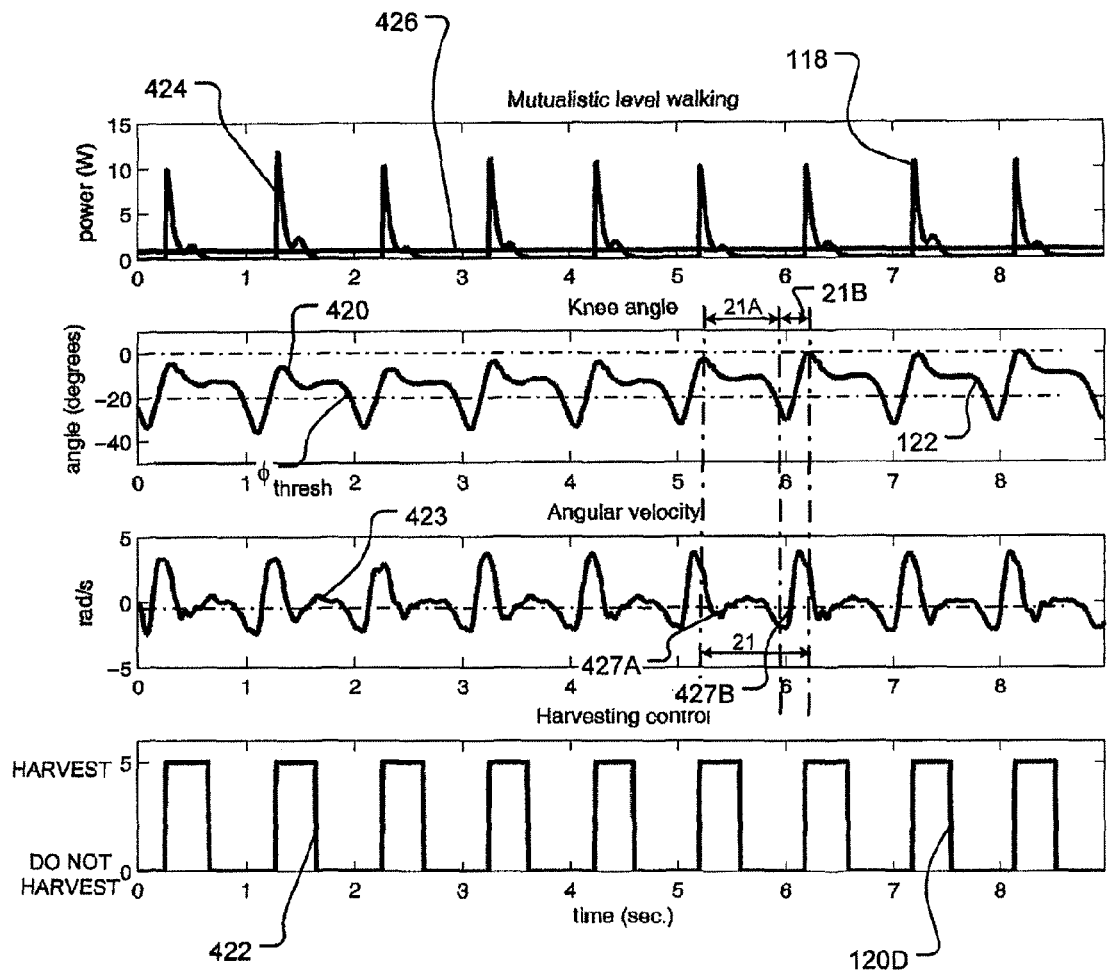
FIG. 16 shows a number of plots relating to the harvesting of energy while the host is walking using the FIG. 13A-13B energy harvesting apparatus in accordance with the method of FIG. 15.

FIG. 15 is a block diagram illustrating a method 400 for predicting the existence of primarily mutualistic conditions. Method 400 is suitable for use with energy harvester 60C of FIGS. 13A, 13B and 14. Those skilled in the art will appreciate, however, that method 400 may be modified for use with other embodiments. FIG. 16 shows a number of plots relating to the harvesting of energy while the host is walking using energy harvester 60C in accordance with method 400. Characteristics of the FIG. 16 plots (e.g. the amplitude and frequency) may vary for each individual host and for the conditions being experienced by a particular host.

Plot 420 shows the angle of knee joint 62 of a particular host during a walking motion. As discussed above, controller 108 may determine the angle of knee joint 62 using feedback signal 122 from sensor(s) 110 (i.e. potentiometer 113 in the illustrated embodiment). When the host is walking, each cycle 21 of plot 402 comprises a stance phase 21A and a swing phase 21B. Plot 423 shows the angular velocity of knee joint 62. The angular velocity plot 423 may be obtained by taking the derivative of the angular position plot 420, for example. Plot 422 represents control signal 120D which, in the illustrated embodiment, is a binary signal having an enable harvest level and a disable harvest level. When plot 422 is at its enable harvest level, controller 108 outputs a signal 120D which causes switch 136 to close. When switch 136 is closed, the motion of knee 62 is coupled to electrical load 111, such that electrical power output signal 118 is delivered to load 111. When plot 422 is at its disable harvest level, controller 108 outputs a signal 120D which causes switch 136 to open, thereby decoupling the motion of knee 62 from electrical load 111 and disengaging energy harvesting.

Method 400 makes use of model-based control. In the illustrated embodiment, method 400 also makes use of sensor(s) which provide information relating to the angular position (or other angular characteristic(s)) of knee 62. In alternative embodiments, method 400 may make use of other sensors that detect one or more characteristics associated with a repetitive motion (e.g. walking). In many respects, model-based control method 400 is similar to model-based control method 200 (FIG. 9). Blocks 402, 404 and 406 are substantially similar to blocks 202, 204 and 206 of model-based control method 200 (FIG. 9) and respectively involve reading feedback signal 122 from angular position sensors 110; processing the newly acquired sensor information; and conducting an inquiry into whether the processed sensor data indicates that knee 62 has just begun the swing phase knee extension.

If the block 406 inquiry indicates that the swing phase knee extension has just begun (block 406 YES output), then method 400 proceeds to block 410 (which imposes a short delay). Block 410 may be similar to block 210 of method 200. From block 410, method 400 proceeds to block 412, where controller 108 commences energy harvesting in a manner similar to block 212 of method 200. Method 400 then loops back to block 402, where controller 108 obtains more angular position data from sensors 110.

The next time method 400 arrives at block 406, the swing phase knee extension will have begun on the previous loop, so method 400 will exit block 406 through the block 406 NO output into block 408. In general, block 408 involves determining whether the energy harvesting engaged in block 212 should be discontinued (e.g. because conditions are no longer mutualistic). Block 408 may be substantially similar to block 208 of method 200.

If the block 408 inquiry indicates that the stance phase knee extension has not just begun (block 408 NO output) and switch 136 is closed (i.e. energy harvester 60C is harvesting energy), then switch 136 remains closed and energy harvester 60C continues to harvest energy while method 400 loops back to block 402. If on the other hand, the block 408 inquiry indicates that stance phase knee extension has just begun (block 408 YES output) and switch 136 is closed (i.e. energy harvester 60C is harvesting energy), then method 400 proceeds to delay block 414. Delay block 414 may be similar to delay block 214 of method 200. Method 400 then proceeds to block 416, where controller 108 disengages energy harvesting in a manner similar to block 216 of method 200. After block 416, method 400 again loops back to block 402. If the block 408 inquiry indicates that stance phase knee extension has not just begun (block 408 NO output) and switch 136 is open (i.e. energy harvester 60C is not harvesting energy), then method 400 loops back to block 402 without changing the status of switch 136.

Like the model-based control methods for harvesting energy during walking shown in FIGS. 9 and 10, model-based control similar to that of FIGS. 15 and 16 may be used for other cyclical movements.

Figure 17:
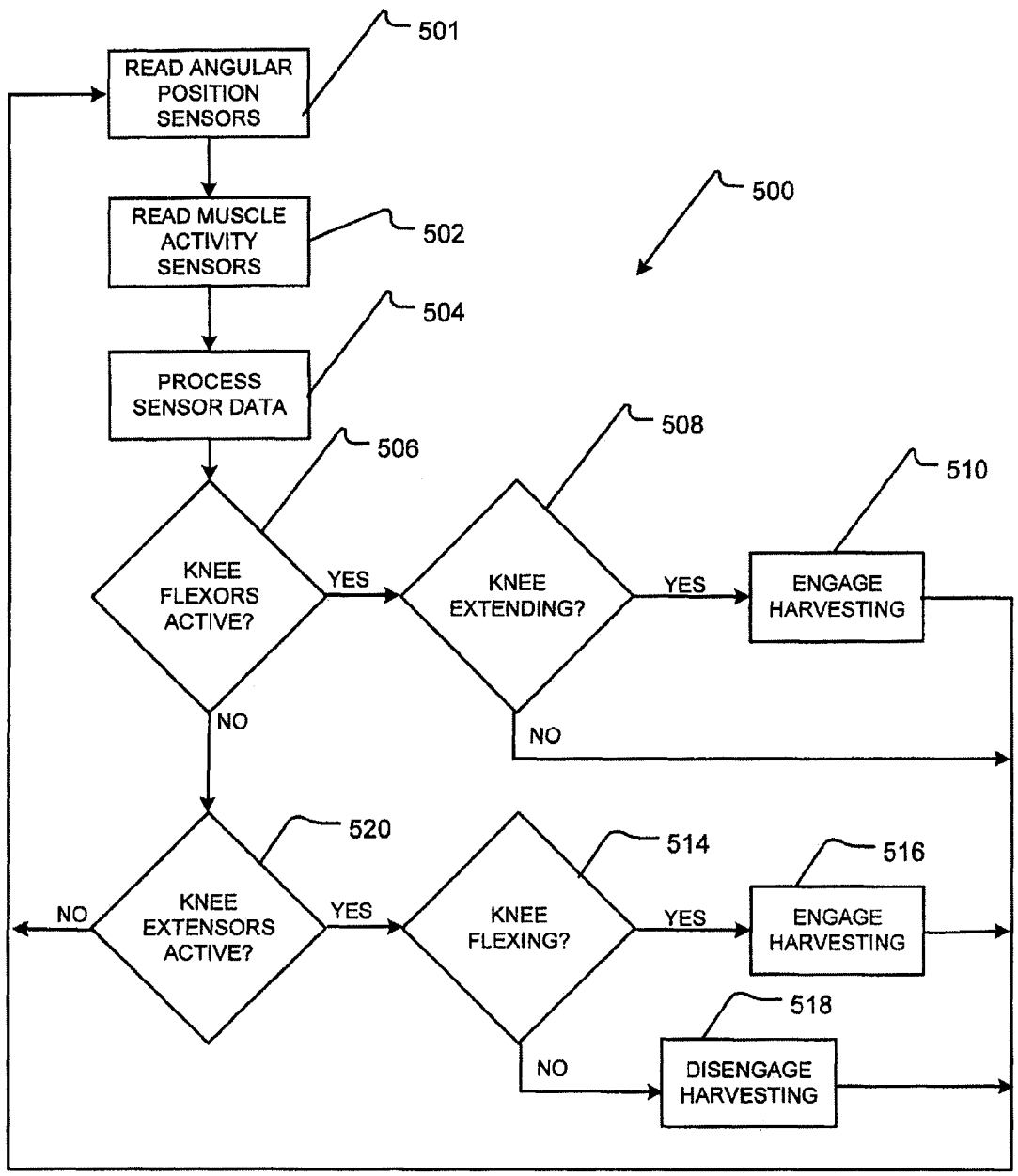
FIG. 17 is a schematic block diagram showing a method for determining when to selectively harvest energy using the FIG. 13A-13B energy harvesting apparatus according to another embodiment of the invention.

FIG. 17 is a block diagram illustrating a method 500 for predicting the existence of primarily mutualistic conditions suitable for use with energy harvester 60C of FIGS. 13A, 13B and 14 using muscle activity-based control. Method 500 makes use of one or more position sensor(s) which provide information relating to the angular position (or other angular characteristic(s)) of knee 62 and a plurality of muscle activity sensor(s) which provide information relating to the activity of the knee flexor muscles and to the activity of the knee extensor muscles. Blocks 501, 502 and 503 of method 500 are similar to blocks 301, 302 and 303 of method 300 and respectively involve obtaining feedback signal 122 from angular position sensor(s) 110, obtaining feedback signal 122 from muscle activity sensor(s) 110; and processing the newly acquired sensor information.

Block 506 involves an inquiry into whether the knee flexor muscles are active. Block 506 may be performed in a manner similar to block 308 of method 300. If the block 506 inquiry indicates that there is an insufficient level of activity in the knee flexor muscles (block 506 NO output), then method 500 proceeds to block 520. On the other hand, if the block 506 inquiry indicates that the knee flexor activity is significant (block 506 YES output), then method 500 proceeds to block 508.

Block 508 involves an inquiry into whether or not knee 62 is extending. The block 508 inquiry may be performed in a manner similar to block 306 of method 300. If the block 508 inquiry indicates that knee 62 is not extending (block 508 NO output), then method 500 loops back to block 501 to collect more data. If on the other hand the block 508 inquiry indicates that knee 62 is extending (block 508 YES output), then method 500 proceeds to block 510, where controller 108 engages harvesting before looping back to block 501 to collect more data. In some embodiments, method 500 may optionally involve delaying for a short period before engaging harvesting in block 510. The amount of such a delay may be constant or may be separately configured (or configurable) for each user. The delay may be related to the period of the walking cycle 21 of a particular host. The delay may be configured to achieve improved performance (e.g. greater power output and/or improved user comfort). Method 500 then loops back to block 501 to obtain more data.

Block 520 involves an inquiry into whether the knee extensor muscles are active. Block 520 may be performed in a manner similar to block 308 of method 300 except that block 520 involves extensor muscles rather than flexor muscles. If the block 520 inquiry indicates that there is an insufficient level of activity in the knee extensor muscles (block 520 NO output), then method 500 loops back to block 501 to collect more data. On the other hand, if the block 520 inquiry indicates that the knee extensor activity is significant (block 520 YES output), then method 500 proceeds to block 514.

Block 514 involves an inquiry into whether or not knee 62 is flexing. The block 514 inquiry may comprise comparing the time derivative of the angular position data (i.e. the angular velocity) to zero. If the angular velocity is less than zero, then knee 62 is flexing. Alternatively, the block 306 inquiry may involve looking at historical angular position data to determine if the current angular position is less than the previous angular position (in which case knee 62 is flexing). If the block 514 inquiry indicates that knee 62 is not flexing (block 514 NO output), then method 500 proceeds to block 518 where controller 108 disengages harvesting (if harvesting was engaged) before looping back to block 501 to collect more data. If on the other hand the block 514 inquiry indicates that knee 62 is flexing (block 514 YES output), then method 500 proceeds to block 516 where controller 108 engages harvesting before looping back to block 501 to collect more data.

It can be see from FIG. 17, that energy harvesting is engaged (in block 510) when knee 62 is extending (block 508 YES output) and the knee flexor muscles are active to decelerate this extension (block 506 YES output). These conditions correspond to mutualistic region 28B. FIG. 17 also shows that energy harvesting is engaged (in block 516) when knee 62 is flexing (block 514 YES output) and the knee extensor muscles are active to decelerate this flexion (block 520 YES output). These conditions correspond to mutualistic region 28A.

Method 500 is configured to engage energy harvesting through regions 28A, 28B and 28C (FIG. 2). After engaging harvesting, method 500 does not disengage harvesting until block 518. Block 518 corresponds to the beginning of the stance phase knee extension (i.e. the beginning of region 22B of plot 22 (FIG. 2) and the end of region 28A of plot 28 (FIG. 2).

In some embodiments, controller 108 can be configured to allow non-mutualistic harvesting. For example, controller 108 can be configured to output the appropriate signal 120A, 120B, 120C, 120D to maintain the engagement between the movement of knee 62 and the electrical load 111. In some embodiments, the control system for selectively engaging and disengaging energy harvesting is removed from any of the above-described embodiments, such that they harvest energy under mutualistic conditions and non-mutualistic conditions. By way of non-limiting example, energy harvesting apparatus 60A (FIG. 8) may be configured to harvest energy under mutualistic and non-mutualistic conditions by configuring controller 108 in a suitable manner or by removing controller 108, switch 136 and/or sensors 110. When modified in this manner, energy harvester 60A still only harvest energy when knee 62 is extending, because of roller clutch 130 (i.e. energy harvester is uni-directional).

Figure 18:
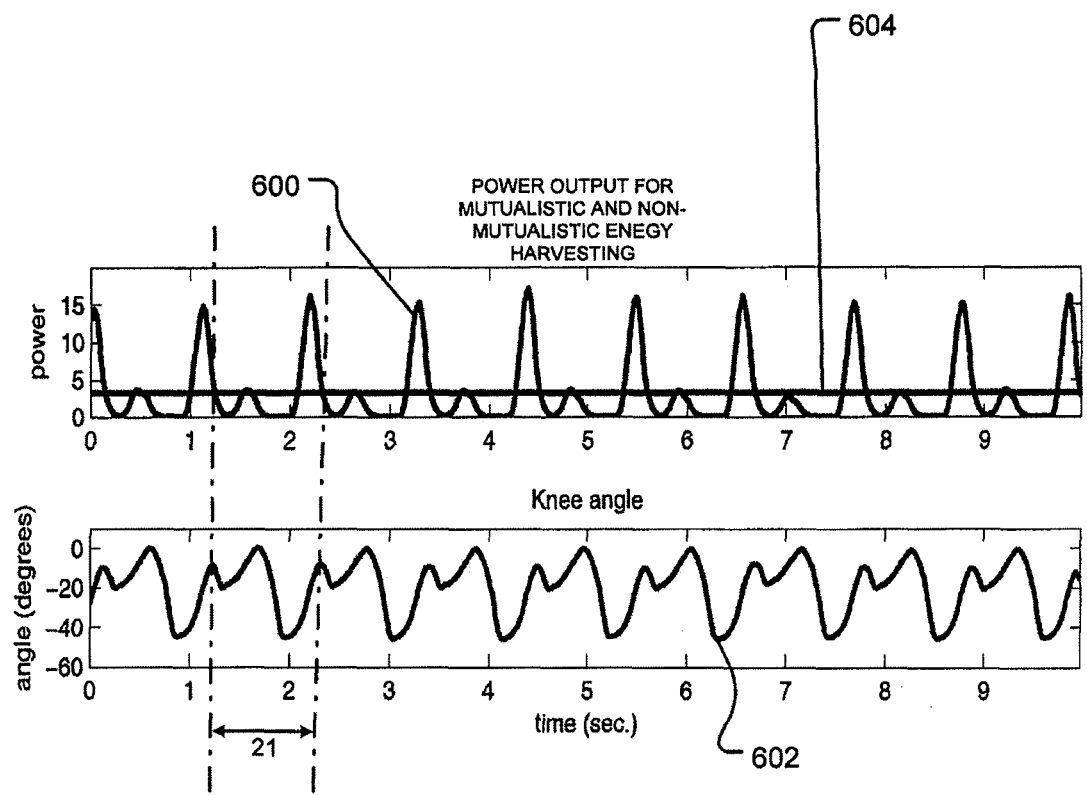
FIG. 18 shows a number of plots relating to the harvesting of energy while the host is walking using the FIG. 6A-6B energy harvesting apparatus configured to harvest energy under mutualistic and non-mutualistic conditions.

While modification of any of the above-described embodiments (or configuring their controllers) to harvest energy under non-mutualistic conditions can still produce a reasonable amount of energy, such energy production will come at the expense of increased effort from the host, as the host will have to exert extra mechanical power to move generator 104 under non-mutualistic conditions. FIG. 18 shows a number of plots relating to the harvesting of energy while the host is walking using energy harvester 60A configured to harvest energy under mutualistic and non-mutualistic conditions. Characteristics of the FIG. 18 plots (e.g. amplitude and frequency) may vary for each individual host and for specific conditions being experienced by a particular host. Plot 602 represents the position of knee 62 (as measured by sensors 110), plot 600 represents the instantaneous output power of signal 118 and plot 604 represents the average output power of signal 118.

FIG. 18 shows that during a typical walking cycle 21 energy harvesting occurs during both periods when knee 62 is extending (i.e. when the slope of plot 602 is positive). Plot 604 indicates that when harvesting under mutualistic and non-mutualistic conditions, the average output power generated at load 111 by energy harvester 60A is 3.2 W which is greater than the 2.4 W output when harvesting under primarily mutualistic conditions (FIG. 10). However, harvesting energy under non-mutualistic conditions requires significant energy input from the host.

Figures 21A, 21B, 21C:
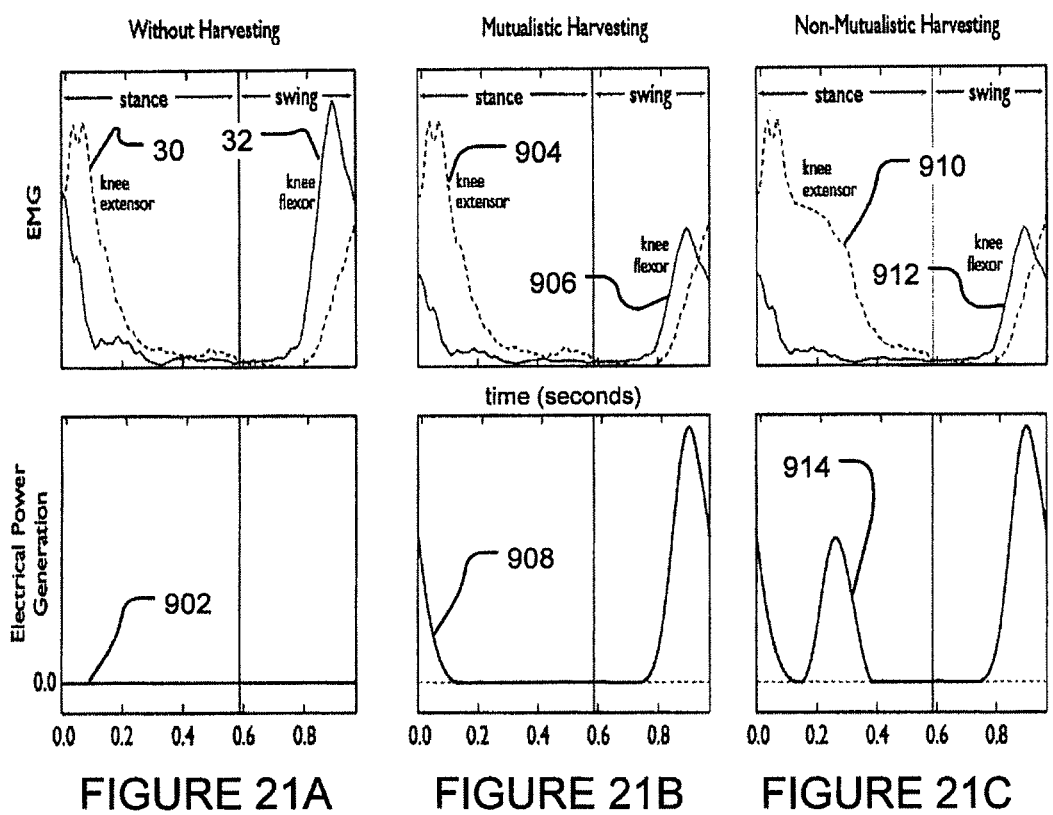
FIGS. 21A, 21B and 21C respectively depict EMG plots showing muscle activity levels and electrical power generation for a human walking with no energy harvesting, with mutualistic energy harvesting (associated with knee extension only) and with both mutualistic and non-mutualistic energy harvesting (associated with knee extension only)

FIGS. 21A, 21B and 21C respectively depict EMG plots showing muscle activity levels and electrical power generation for a human walking. FIG. 21A depicts EMG plots 30 for knee extensor muscles and 32 for knee flexor muscles and electrical power plot 902 for a human walking with no energy harvesting. FIG. 21B depicts EMG plots 904 for knee extensor muscles and 906 for knee flexor muscles and electrical power plot 908 for a human walking with mutualistic energy harvesting associated with knee extension only. FIG. 21C depicts EMG plots 910 for knee extensor muscles and 912 for knee flexor muscles and electrical power plot 914 for a human walking with both mutualistic and non-mutualistic energy harvesting associated with knee extension only (i.e. when the motion of the knee in the extension direction is always coupled to the electrical load).

It can be seen (by comparing plot 906 of FIG. 21B with plot 32 of FIG. 21A) that mutualistic energy harvesting during knee extension reduces the knee flexor activity associated with decelerating the knee extension. Plot 908 shows that electrical energy is generated during mutualistic energy harvesting. It can also be seen (by comparing plot 910 of FIG. 21C with plot 904 of FIG. 21B) that non-mutualistic energy harvesting during knee extension increases knee extensor activity associated with moving the knee during the stance phase knee extension. Comparing plot 914 and plot 908 shows that more electrical energy is generated when harvesting energy during mutualistic and non-mutualistic conditions (relative to mutualistic conditions only), but that this excess electrical energy harvesting comes at the expense of extra effort from the knee extensor muscles.

Figure 22:
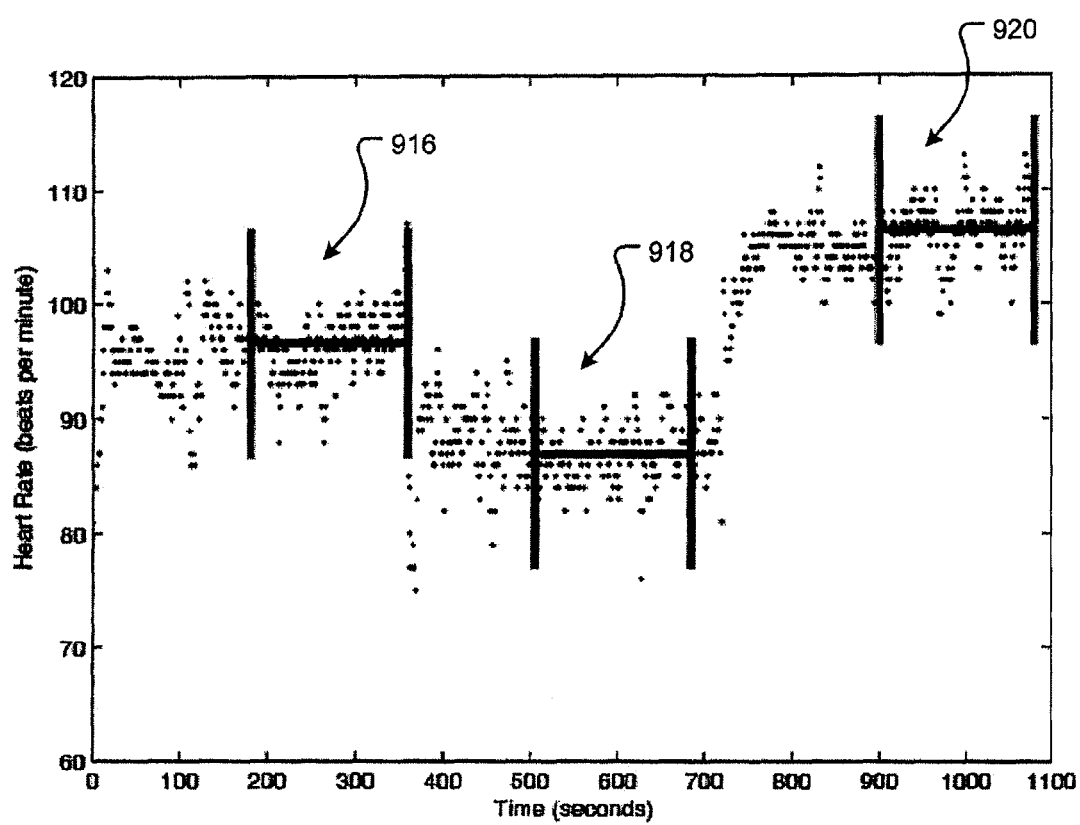
FIG. 22 shows a plot of heart rate versus time for a human walking with no energy harvesting, with mutualistic energy harvesting (associated with knee extension only) and with both mutualistic and non-mutualistic energy harvesting (associated with knee extension only).

FIG. 22 shows a plot of heart rate versus time for a human walking with no energy harvesting (region 916), with mutualistic energy harvesting associated with knee extension only (region 918) and with both mutualistic and non-mutualistic energy harvesting associated with knee extension only (region 920). Heart rate is a general indicator of the physical effort involved with an associated activity. Comparing region 916 and region 918 of FIG. 22 shows that less effort is required to walk when harvesting energy under mutualistic conditions (region 918) than is required to walk without harvesting energy (region 916). Comparing region 920 to regions 916 and 918 of FIG. 22 shows that more effort is required to walk when harvesting energy under mutualistic and non-mutualistic conditions (region 920) than is required to walk without harvesting energy (region 916) or than is required to walk while harvesting energy under mutualistic conditions (region 918).

As shown in FIG. 4B, energy harvesting apparatus 70 may be provided as part of, or as an addition to, an orthopedic prosthesis 74. In the illustrated embodiment, energy harvester 70 harvests energy across a joint 72 (or joints) between segments 74A, 74B of prosthesis 74 in order to harvest mechanical energy transmitted by joint 72 in much the same manner that any of the above-described energy harvesting apparatus. Energy harvester 70 may incorporate components that are similar to those of the above-described energy harvesting apparatus. Energy harvester 70 may be integrated with prosthesis 74. Preferably, energy harvester 70 harvests energy under primarily mutualistic conditions. Energy harvester 70 may be provided with a control mechanism that permits a user to engage or disengage energy harvesting and/or to change an operational mode of energy harvester 70.

In the illustrated embodiment, energy harvester 70 is used in connection with a prosthesis wherein joint 72 is a knee joint (FIG. 4). Knee joints of prosthetic limbs are typically braked (i.e. decelerated) by passive devices, such as hydraulics (e.g. Ossur™ Total Knee), or by active devices, such as a Magnetorheologic (MR) Fluid Actuator (e.g. Ossur™ Rheo Knee). Energy harvester 70 uses a generator similar to generator 104 to perform negative work on joint 72, thereby decelerating the motion of joint 72. The generator converts this mechanical energy into electrical energy which may be used, in whole or in part, to power electrical components (not shown) of prosthesis 74. Harvesting energy in this manner can greatly increase the efficiency of prosthesis 74, allowing for smaller, lighter batteries and longer periods between charges.

Energy harvester 70 may comprise a controller similar to controller 108 which may selectively engage motion of joint 72 to an electrical load under mutualistic conditions. Energy harvester 70 may comprise one or more sensors (similar to sensors 110) to detect the angular position of joint 72. Such sensors may also detect information in respect of an actuator (not shown) acting at joint 72. For example, such sensors may detect information, such as current draw for a MR Fluid Actuator or force and velocity signals from a hydraulic actuator, and the controller may use this information to make decisions as to when conditions are mutualistic.

In some embodiments, energy harvester 70 is used in the place of the conventional actuator for joint 72 of prosthesis 74. Energy harvester 70 may be selectively engaged and disengaged at the correct part of the walking step cycle based on feedback signals related to joint angular velocities, ground reaction force under the prosthetic leg, and information from the intact leg, for example. Exemplarily control logic for an embedded energy harvester is illustrated in FIG. 12.

Figure 19:
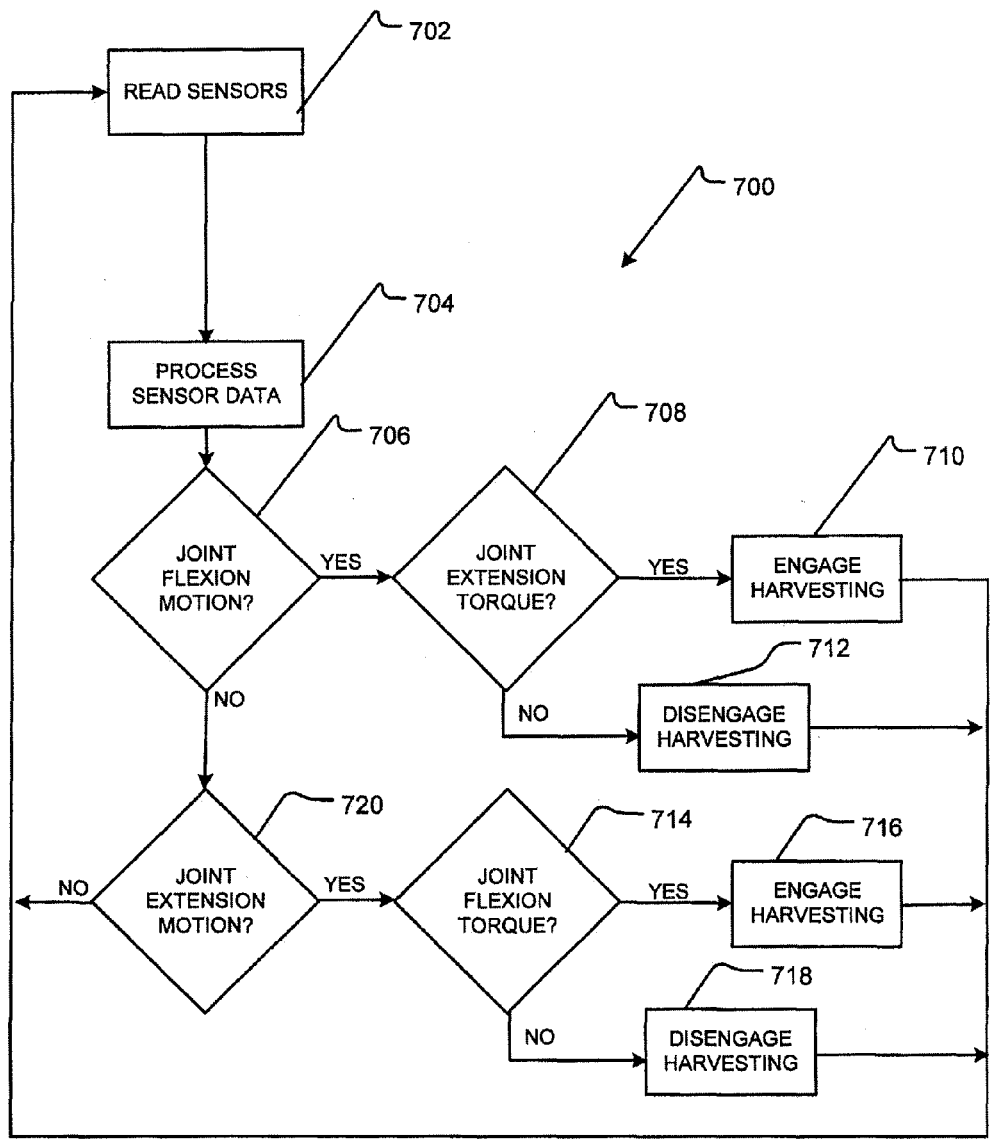
FIG. 19 is a schematic block diagram showing a method for determining when to selectively harvest energy using the FIG. 4B energy harvesting apparatus according to a particular embodiment of the invention.

FIG. 19 schematically depicts a method 700 for controlling energy harvester 70 so that it will harvest energy during primarily mutualistic conditions. Method 700 involves reading available sensor data in block 702 and processing the sensor data in block 704. Blocks 706, 708, 714 and 720 involve using the processed sensor data to make determinations about the direction of motion of joint 72 and the net torque on joint 72. FIG. 19 shows that the energy is harvested (block 710) when joint 72 is moving in an flexion direction (block 706 YES output) and the net torque on joint 72 is in an extension direction (block 708 YES output). Similarly, energy is harvested (block 716) when joint 72 is moving in an extension direction (block 720 YES output) and the net torque on joint 72 is in a flexion direction (block 714 YES output).

FIG. 4C depicts an energy harvesting apparatus 80 according to another embodiment of the invention wherein energy harvesting apparatus 80 is implanted within the body of the host. In the illustrated embodiment, energy harvester 80 is placed across the anterior aspect of the ankle joint 82 with an anatomical location similar to that of the tibialis anterior muscle 84. In other embodiments, energy harvester 80 could be configured to work in conjunction with another joint (or joints) between corresponding body segments. Energy harvester 80 may be configured to harvest energy in a mutualistic mode and to thereby assist a specific muscle (or group of muscles) during the phases in which the muscle(s) operate in negative mechanical power modes. In some embodiments, energy harvester 80 may be configured to also harvest energy during non-mutualistic modes or to cease energy harvesting altogether. Switching between operational modes may be accomplished by the user, as desired, using a remote switch (not shown), for example.

In general, the components and operation of implanted energy harvester 80 may be similar to those of energy harvesters 60, 60A, 60B, 60C and 70 described above. In some embodiments, the generator (not shown) of energy harvester 80 comprises a piezoelectric generator to convert mechanical displacement in to electrical energy. In such embodiments, load leveling and gearing may not be required. In the illustrated embodiment, one end of the generator is attached to the shin bone and the other end to a foot bone. This may be done, for example, using bone screws made of suitable bio-compatible material(s), such as tantalum—a relatively strong material that is not rejected by the body. Some of the components of energy harvester 80 (e.g. the controller and power conditioning circuitry) may be housed in a small implanted hermetic container (not shown). The container may be made, for example, of titanium or some other suitable bio-compatible material.

To operate in a mutualistic mode, the controller of energy harvester 80 uses information from suitable sensors to determine when the muscle it is aiding is operating in a negative mechanical power mode. As discussed above, a muscle operates in a negative mechanical power mode when the muscle is lengthening and the muscle is active (i.e trying to contract). The velocity of the muscle can be sensed, for example, using accelerometers implanted in the muscle and the activity of the muscle can be sensed, for example, using EMG electrodes implanted in the muscle. Signals from these sensors may be conducted back to the implanted controller by way of suitable conductors such as Teflon™-coated wires.

Figure 20:
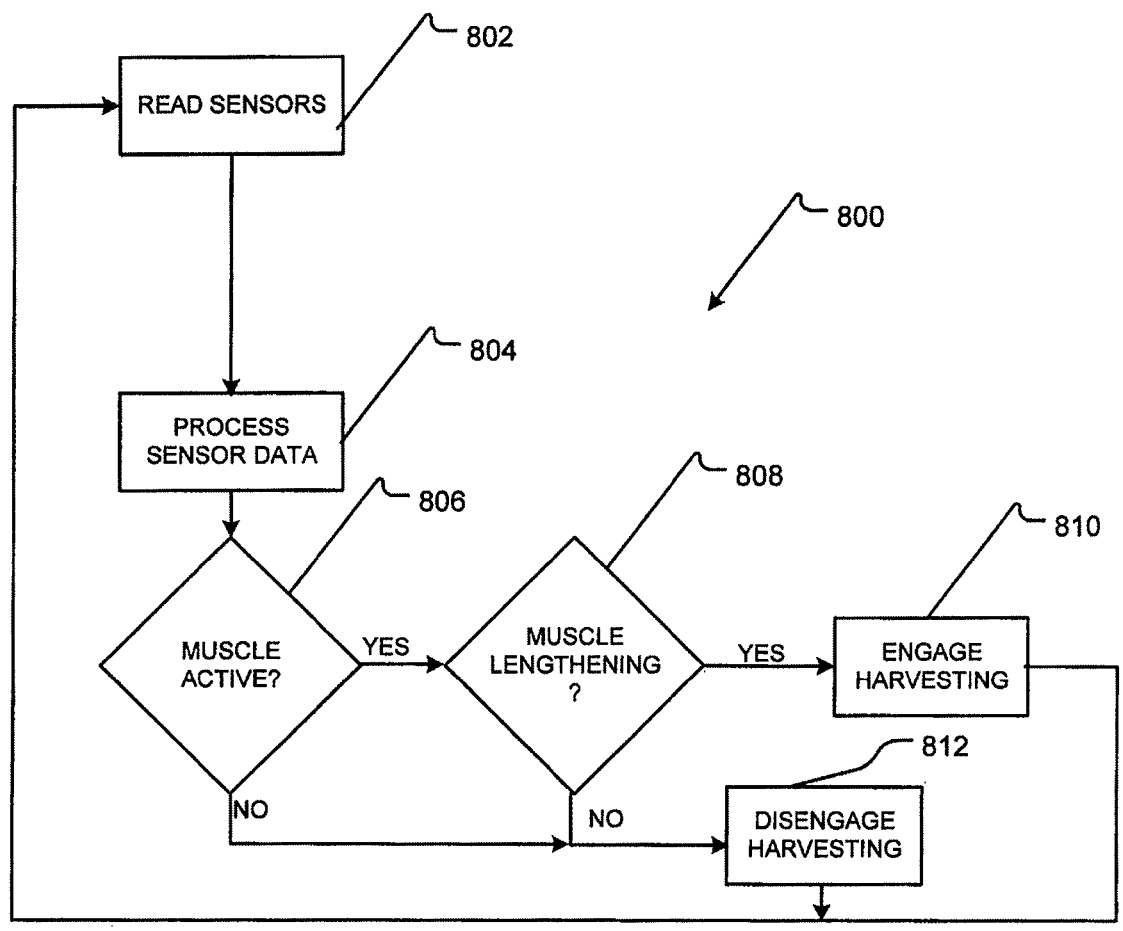
FIG. 20 is a schematic block diagram showing a method for determining when to selectively harvest energy using the FIG. 4C energy harvesting apparatus according to a particular embodiment of the invention.

The controller of energy harvester 80 may be configured to engage harvesting when the associated muscle is active and the muscle is lengthening. FIG. 20 is a schematic block diagram showing a method for determining when to selectively cause energy harvesting apparatus 80 to harvest energy according to a particular embodiment of the invention. Method 800 senses data (block 802) and processes the incoming data (block 804). Method 800 engages harvesting (block 810) when the muscle is active (block 806 YES output) and when the associated muscle is lengthening (block 808 YES output). Otherwise harvesting is disengaged (block 812).

In the illustrated embodiment, the controller of energy harvester 80 may be configured to harvest energy when tibialis anterior muscle 84 is active and tibialis anterior muscle 84 is lengthening. The resulting electrical energy produced by harvester 80 may be used to charge a battery and/or used directly to power another implanted device. For example, the electrical power may be used to charge a small storage battery, such as a lithium-iodine battery, that may be contained within the box that contains the controller.

During walking, energy harvester 80 operates as follows. When the leg is in middle of its swing phase, the electrical load is disengaged from movement about the ankle. Just prior to heel-strike, the tibialis anterior muscle is activated which is sensed using one or more muscle activity sensors. This activity in the tibialis anterior muscle meets one condition for engaging energy harvesting. At heel-strike, the tibialis anterior muscle is lengthened which is sensed using one or more accelerometers or other suitable sensor(s). This lengthening of the tibialis anterior muscle meets the second condition for energy harvesting. The controller then couples the electrical load to the movement of ankle 82. As the stance phase progresses, the sensors detect that the tibialis anterior muscle stops lengthening, causing the controller to disengage energy harvesting.

While a number of exemplary aspects and embodiments have been discussed above, those of skill in the art will recognize certain modifications, permutations, additions and sub-combinations thereof. For example:

- Some of the embodiments described above involve selectively harvesting energy in a mutualistic mode using the muscles associated with the knee of a human. Those skilled in the art will appreciate that selectively harvesting energy in a mutualistic mode from the muscle(s) associated with other joints is considered to be within the scope of the invention. By way of non-limiting example, one may design similar systems to harvest energy from the muscles associated with movement of an ankle, shoulder, elbow, finger, wrist, neck, hip or the like. Also, energy harvesters according to other embodiments are configured to extract energy from a plurality of joints.
- Some of the embodiments described above involve selective energy harvesting in a mutualistic mode during particular movements, such as walking. In other embodiments, selective energy harvesting in a mutualistic mode may be provided for other types of movements. By way of non-limiting example, such movements may involve knee bends, descending stairs or sloped surfaces, cycling, dancing, typing, throwing or the like.
- In addition to operating in a mutualistic mode, any of the above-discussed embodiments may be configured to operate in a non-mutualistic mode, where electrical energy is harvested at the expense of additional effort required by the host. A benefit of non-mutualistic mode energy harvesting is that there may be more power available for harvesting when compared to mutualistic mode energy harvesting alone.
- The electrical energy generated by any of the above-discussed embodiments may be used in any suitable manner. For example, this electrical energy may be used directly to power electrical devices or this electrical energy may be stored for later use. Non-limiting examples of electrical devices which may be powered by the electrical energy generated by the above-discussed embodiments include orthopedic or neural prosthetic devices, and portable electronic devices (e.g. cellular telephones, personal digital assistants, global positioning system receivers, laptop computers or the like).

Some of the embodiments described above make use of a roller clutch as a uni-directional torque transfer mechanism. In alternative embodiments, other suitably configured, uni-directional torque transfer mechanisms, such as a ratchet mechanism or the like, may be used in place of a roller clutch.

Bi-directional energy harvesting apparatus (e.g. energy harvester 60C of FIGS. 13A, 13B and 14) may be configured to have different gear ratios for flexion and extension. Such different gear ratios may compensate for circumstances where the mechanical power input tends to have different torques and/or different velocities in either direction.

It is not necessary that bi-directional energy harvesting apparatus incorporate a mechanical rectifier. Rectification may be performed in the electrical domain. For example, uni-directional energy harvester 60A may be made bi-directional by simply removing roller clutch 130 and modifying rectifier 138 to accommodate bidirectional electrical output from generator 104.

Bi-directional energy harvesting apparatus 60C (FIG. 14) is described as having a electronic switch 136 for coupling the body 61 of the host to electrical load 111 and for decoupling the body 61 of the host from electrical load 111. In other embodiments, energy harvester 60C comprises a controllable mechanical clutch or the like (similar to clutch 150 if energy harvester 60B (FIG. 12) for coupling the body 61 of the host to electrical load 111 and for decoupling the body 61 of the host from electrical load 111. Such a controllable clutch could be located between mechanical connection 100 and mechanical rectifier 164 or between mechanical rectifier 164 and gearing 134, for example. Controller 108 may control such a controllable clutch using a corresponding signal 120B.

Some embodiments may comprise different generator types or different generator components. For example, it may be beneficial to use an electro-active polymer or piezo-electric generator. In some embodiments, the generator may generate electricity in response to linear motions of generator components relative to one another. It may also be beneficial to use two or more generators.

Some embodiments may comprise different transmission configurations or different transmission components. Gearing may be driven directly (rather than using roller clutches). Mechanisms other than traditional gears may be used to change the torque and speed characteristics of the input mechanical power. Examples of such mechanisms include a capstan drive or lever arm. Other load leveling mechanisms may be used, such as a flywheel, for example. In some embodiments, load levelling and/or gearing are not required. In other embodiments, the gearing serves to decrease the velocity of the input mechanical power, which may be desirable when using certain generators such as piezoelectric generators, for example.

Energy harvesting apparatus 60, 60A, 60C may be modified to add load leveling mechanisms similar to load leveling mechanism 156 of energy harvesting apparatus 60B. For example, energy harvester 60A (FIG. 8 could be modified to provide a load leveling device at line 142 (i.e. between roller clutch 130 and gearing 134, for example. Such load leveling devices could be used to deliver relatively continuous mechanical power to their corresponding gearing 134 and generators 104.

Method 400 (FIG. 15) and method 500 (FIG. 17) describe techniques for harvesting energy associated with knee extension and with knee flexion. Both of these methods involve harvesting energy in the small non-mutualistic region 28C of plot 28 (see FIG. 2). Either of these methods could be modified to harvest energy only in exclusively mutualistic regions (e.g. regions 28A, 28B of plot 28). For example, method 500 could be modified to harvest energy exclusively in mutualistic regions by providing a disengage harvesting block (similar to block 518) on the NO output of blocks 508 and 520.

Delays similar to blocks 210 and 214 of method 200 may be incorporated into other embodiments. By way of non-limiting example, a similar delay could be inserted between blocks 308 and 310 of method 300 (FIG. 11) and/or between blocks 308 and 312 of method 300 and/or between blocks 306 and 312 of method 300. Delays could similarly be inserted into methods 500 (FIG. 17), 700 (FIG. 19), 800 (FIG. 20) and any other embodiment.

Thresholds used to assess whether conditions are mutualistic or non-mutualistic (e.g. $\phi_{thresh}$ and $I_{thresh}$) may be constant or variable and may also be user configurable. Such thresholds may be related to the slope of the terrain. Such thresholds may be adaptive. By way of non-limiting example, if the slope of the terrain changes or the period of a repetitive motion changes, then the threshold may change accordingly.

In some embodiments, the electrical coupling between generator 104 and load 118 may comprise a wireless coupling. For example, electrical power signal 116 or 118 could be transmitted by way of an RF transmitter to a load 111 equipped with a suitable RF receiver.

The above described embodiments comprise a controller 108. In other embodiments, a other control circuits may be used to provide the functionality of controller 108. Such other control circuits may comprise analog electronic circuitry and/or digital electronic circuitry and may comprises a controller of the type described above. The invention should be understood to include any control circuit capable of performing the functions of controller 108 described above.

An energy harvesting device according to the invention may be built into a garment or made to be worn under or over a garment.

The embodiments described above relate to harvesting energy from humans, but those skilled in the art will appreciate that energy could be harvested from animals (e.g. livestock) in accordance with the above-described methods and apparatus.

Accordingly, the scope of the invention should be construed in accordance with the substance defined by the following claims.

What is claimed is:

1. An apparatus for harvesting energy from motion of one or more human or other animal joints, the apparatus comprising:
    a generator for converting mechanical energy into corresponding electrical energy;
    one or more sensors for sensing one or more corresponding characteristics associated with the motion of the one or more joints, wherein at least one of the one or more sensed characteristics is indicative of an angular characteristic of at least one of the one or more joints;

a first coupling operatively connected between the one or more joints and the generator for transferring mechanical energy associated with motion of the one or more joints to the generator;

a second coupling operatively connected between the generator and a load for transferring electrical energy output of the generator to the load; and a control circuitry connected to receive the one or more sensed characteristics and configured, based on the one or more sensed characteristics, to disengage at least one of:

the mechanical energy transfer of the first coupling; and
the electrical energy transfer of the second coupling.

2. The apparatus according to claim 1 wherein the first coupling comprises a uni-directional torque transfer mechanism which is engaged during motion of at least one of the one or more joints in a first angular direction and is disengaged during motion of the at least one of the one or more joints in a second angular direction opposite the first angular direction.

3. The apparatus according to claim 1 wherein the first coupling comprises a transmission for altering torque and speed characteristics of the mechanical energy associated with the motion of the one or more joints prior to transferring this mechanical energy to the generator.

4. The apparatus according to claim 1 wherein the first coupling comprises a load leveling device for adjusting temporal fluctuations in the mechanical energy associated with the motion of the one or more joints prior to transferring this mechanical energy to the generator.

5. The apparatus according to claim 1 wherein the control circuitry is configured, based on the one or more sensed characteristics and after disengaging the at least one of the mechanical energy transfer of the first coupling and the electrical energy transfer of the second coupling, to re-engage the at least one of the mechanical energy transfer of the first coupling and the electrical energy transfer of the second coupling.

6. The apparatus according to claim 1 wherein the first coupling comprises a mechanical rectifier connected such that motion of at least one of the one or more joints in a first direction causes corresponding motion of a mechanical rectifier output component in a corresponding first direction and motion of the at least one of the one or more joints in a second direction opposed to the first direction causes corresponding motion of the mechanical rectifier output component in the corresponding first direction.

7. The apparatus according to claim 1 wherein the control circuitry is configured to generate an output signal based at least in part on the one or more sensed characteristics and connected to provide the output signal to the first coupling to thereby selectively engage and disengage the mechanical energy transfer of the first coupling.

8. The apparatus according to claim 1 wherein the control circuitry is configured to generate an output signal based at least in part on the one or more sensed characteristics and connected to provide the output signal to the second coupling to thereby selectively engage and disengage the electrical energy transfer of the second coupling.

9. The apparatus according to claim 1 wherein the second coupling comprises a switch which, when closed, transfers electrical energy output from the generator to the load and, when open, decouples the transfer of electrical energy output from the generator to the load.

10. The apparatus according to claim 9 wherein the switch is configurable between its open and closed configurations in response to an output signal generated by the control circuitry.

11. The apparatus according to claim 1 wherein the control circuitry is configured to assess whether the motion of the one or more joints is associated with mutualistic conditions or non-mutualistic conditions based at least in part on the one or more sensed characteristics and selectively engage energy harvesting when motion of the one or more joints is associated with particular mutualistic conditions and to selectively disengage energy harvesting when motion of the one or more joints is associated with non-mutualistic conditions.

12. The apparatus according to claim 1 wherein the control circuitry is configured to process the at least one of the one or more sensed characteristics to obtain at least one of: an angular position of the at least one of the one or more joints and an angular velocity of the at least one of the one or more joints.

13. The apparatus according to claim 12 wherein the control circuitry is configured to selectively engage energy harvesting and to selectively disengage energy harvesting based at least in part on detecting zero crossings of the angular velocity of the at least one of the one or more joints.

14. The apparatus according to claim 12 wherein the control circuitry is configured to selectively engage energy harvesting and to selectively disengage energy harvesting based at least in part on comparing the angular position of the at least one of the one or more joints to one or more threshold levels.

* * * * *